(12) United States Patent
Wang

(10) Patent No.: US 6,514,762 B1
(45) Date of Patent: Feb. 4, 2003

(54) DELIVERY OF NUCLEOTIDES BY ELECTROCHEMICAL RELEASE

(75) Inventor: Joseph Wang, Las Cruces, NM (US)

(73) Assignee: New Mexico State University Technology Transfer Corporation, Las Cruces, NM (US)

(*) Notice: Subject to any disclaimer, the term of this patent is extended or adjusted under 35 U.S.C. 154(b) by 0 days.

(21) Appl. No.: 09/553,787

(22) Filed: Apr. 21, 2000

Related U.S. Application Data

(60) Provisional application No. 60/130,749, filed on Apr. 23, 1999, and provisional application No. 60/137,059, filed on Jun. 1, 1999.

(51) Int. Cl.$^7$ .......................... C12N 13/00; C12N 15/64
(52) U.S. Cl. ....................... 435/461; 435/470; 536/25.4
(58) Field of Search ............................ 435/6, 446, 461, 435/470; 536/23.1, 24.3, 25.3, 25.4

(56) References Cited

U.S. PATENT DOCUMENTS

| | | | |
|---|---|---|---|
| 5,892,071 A | | 4/1999 | Nantz et al. |
| 5,908,635 A | | 6/1999 | Thierry |
| 5,952,654 A | * | 9/1999 | Giese .......................... 250/288 |
| 5,964,726 A | | 10/1999 | Korenstein et al. |
| 5,993,434 A | | 11/1999 | Dev et al. |
| 6,014,584 A | | 1/2000 | Hofmann |
| 6,022,735 A | | 2/2000 | Curiel et al. |
| 2002/0061589 A1 | * | 5/2002 | King et al. .................. 435/446 |

OTHER PUBLICATIONS

Adam B. Steel et al., Electrochemical Quantitation of DNA Immobilized on Gold, Analytical Chemistry, vol. 70, No. 22, Nov. 15, 1998, pp. 4670–4677.*
Pankaj Singhal et al., Ultrasensitive Voltammetric Detection of Underivatized Oligonucleotides and DNA, Analytical Chemistry, vol. 69, No. 23, Dec. 1, 1997, pp. 4828–4832.*
F. Jelen et al., Nucleotide Sequence–Dependent Opening of Double–Stranded DNA at an Electrically Charged Surface, Gen. Physiol. Biophys. (1985), 4, pp. 219–237.*
Jaroff, L., "Fixing the Genes," *Time Magazine*, pp 68–73 (Jan. 11, 1999).

Korri–Youssoufi, H., et al., "Toward Bioelectronics: Specific DNA Recognition Based on an Oligonucleotide–Functionalized Polypyrrole," *J. Am. Chem. Soc.*, vol. 119, pp 7388–7389 (1997).
Neumann, E., et al., "Gene Transfer into Mouse Lyoma Cells by Electroportation in High Electric Fields," *Embo Journal*, vol. 1, No. 7, pp 841–845 (1982).
Russo, E., "New Gene Therapy Systems: Advancement in Drug Delivery," *The Scientist* (Feb. 1, 1999).
Wang, J., et al., "Electrochemically Induced Release of DNA from Gold Ultramicroelectrodes," *ASC J. of Surfaces and Colloids—Langmuir*, vol. 15, pp 6541–6545 (1999).
Wang, J., et al., New Label–Free DNA Recognition Based on Doping Nucleic–Acid Proges within Conducting Polymer Films, *Anal. Chim. Acta*, vol. 401, pp 7–12 (1999).
Johnson, Dennis C., et al., "Liquid Chromatography with Pulsed Electrochemical Detection at Gold and Platinum Electrodes", *Analytical Chemistry*, May 15, 1990, pp. 589A–597A, vol. 62, No. 10.
LaCourse, William R., et al., "Optimization of Waveforms for Pulsed Amperometric Detection of Carbohydrates Based on Pulsed Voltammetry", *Analytical Chemistry*, Jan. 1, 1993, pp. 50–55, vol. 65, No. 1.
Pang, Dai–Wen, et al., "Electrochemical Oxidation of DNA at a Gold Microelectrode", *Electroanalysis*, 1995, pp. 774–777, vol. 7, No. 8.

* cited by examiner

Primary Examiner—James Ketter
(74) Attorney, Agent, or Firm—Stephen A. Slushner; Nancy E. Ownbey

(57) ABSTRACT

An apparatus and method for controlled release of nucleotides from electrodes utilizing potential difference for use in delivering the nucleotide into an organism. The frequency, duration and rate of release may be specifically controlled to obtain optimal release of the nucleotide. The apparatus and method may be used in conjunction with methods for electroporation, wherein the nucleotide may transit the cell membrane, and move into the cell. Alternatively, the apparatus and method may be used in conjunction with complexes of DNA and lipids or other carriers, which complexes will transit the cell membrane and move into the cell. The apparatus and method may be used for gene therapy, for use in treatment of any of a wide variety of diseases.

30 Claims, 11 Drawing Sheets

DELIVERY OF NUCLEOTIDES BY ELECTROCHEMICAL RELEASE

CROSS-REFERENCE TO RELATED APPLICATIONS

This application claims the benefit of the filing of U.S. Provisional Patent Application Serial No. 60/130,749, entitled Electrochemically-Induced Release of Nucleic Acids (Gene Therapy), filed on Apr. 23, 1999, and U.S. Provisional Patent Application Serial No. 60/137,059, entitled Controlled Release of DNA from Carbon Paste Electrodes, filed on Jun. 1, 1999, and the specification thereof of each is incorporated herein by reference.

GOVERNMENT RIGHTS

The U.S. Government has a paid-up license in this invention and the right in limited circumstances to require the patent owner to license others on reasonable terms as provided for by the terms of Grant No. 1-RO1-RR14549-01 awarded by the U.S. National Institutes of Health of the Department of Health and Human Services.

BACKGROUND OF THE INVENTION

1. Field of the Invention (Technical Field)

The present invention relates to an apparatus and methods for controlled electrochemical release of DNA and other nucleic acids from electrodes, for use in cellular transfection, including gene therapy, and for other applications of controlled release of DNA and other nucleic acids.

2. Background Art

There is significant interest in controlled gene delivery for gene therapy in treatment of a wide variety of genetic diseases. In one mode of effecting gene therapy, macromolecules, generally DNA, are introduced into the cell. The cells are then transfected with the DNA, leading to transformed viable cells. Normal and functional genetic material is introduced into cells to correct an abnormality due to a defective or deficient gene product. Typically, the transferred genetic material contains the desired gene and a promoter to control the expression of the gene.

Nucleic acids as therapeutically effective substances are also used to inhibit specific cell functions. For example, antisense RNA and DNA sequences can be employed for selective inhibition of specific gene sequences. The antisense sequences act by blocking the expression of certain genes (such as deregulated oncogenes or viral genes) within the cell. The efficacy of short sequence antisense oligonucleotides has been demonstrated, even at low or comparatively low concentrations within the cell.

While significant progress has been made in manipulating genes at a cellular level, gene therapy for treatment of disease is limited and not commercially developed. There are a number of factors limiting effective gene therapy, including the number and rate of transformed cells required for a therapeutic effect. Efficiencies of transfection and transformation are related, in part, to the mode of delivery of the genetic material to and into the cell.

There are a number of methods that have been developed for the delivery of genetic material to and into the cell. These include a variety of physical delivery methods. Methods of physical delivery methods include electroporation; cell bombardment by coated molecules (called a "gene gun"); use of chemicals to increase cell membrane permeability, such as detergents or polyethyleneglycol; and various lipid-based techniques, such as liposome-cell fusion.

Electroporation utilizes short, high voltage electrical pulses to produce a transient high permeability state in cell membranes. The cells are exposed to exogenous DNA in high electric fields, with transference of DNA through the transient permeable hydrophilic pores. Electroporation techniques are taught in a number of patent applications, including U.S. Pat. Nos. 5,019,034, 5,749,847, 5,869,326, 5,993,434, and 6,014,584. Related techniques are taught in, for example, U.S. Pat. Nos. 4,081,340 and 5,964,726.

Another approach in gene therapy has been to use a gene spliced into a virus, such as a retrovirus or adenovirus, as a vector to introduce the gene into the target cell. This approach, however, has significant limitations, including safety and efficiency. In some applications, the approach requires the multiplication of target cells in vitro and subsequent reintroduction of the transformed cells. Even where the virus is introduced by direct administration of viral particles, there are other limitations to the approach. The size of the gene that can be carried by the viral vector is limited, and the genetic material that can be incorporated is similarly limited to DNA. Thus viral delivery approaches cannot be utilized with other nucleotides. Modifications of use of viruses in gene therapy, including use of non-viral sequences that bind cell membrane receptors, have also been explored. See, for examples, U.S. Pat. Nos. 5,916,803 and 6,022,735 and patents and publications cited therein.

A variety of lipid-based techniques have been employed, including use of liposomes. These methods are generally described in U.S. Pat. Nos. 5,892,071 and 5,908,635 and patents and publications cited therein.

With each of the methods, and particularly the physical delivery methods, there is a need to have the DNA, RNA or other nucleotide in immediately proximity to the cell membrane to be transited.

SUMMARY OF THE INVENTION (DISCLOSURE OF THE INVENTION)

The invention includes a method for controlled nucleotide release, in which nucleotides to be released are first adsorbed on to at least one first electrode. A second electrode is provided, and the first and second electrodes are immersed in an aqueous media in which the nucleotide is to be released. A negative electrical charge is then applied to the first electrode relative to the second electrode, and the resulting release of nucleotide is proportional to the relative electrical charge difference and length of persistence of the charge difference. In this method, more than one first electrode may be employed, so that there may be two or more electrodes to which nucleotides are adsorbed, with one second electrode.

The step of adsorbing can be facilitated by applying a positive potential to the first electrode relative to the second electrode. Alternatively, the nucleotide may be adsorbed by incubation of the electrode in a solution containing the nucleotides for a suitable period. In the method, a third electrode can also be provided, where the second electrode serves as a counter electrode, and the third electrode serves as a reference electrode. In a preferred embodiment, the negative electrical charge is a potential difference of from about −0.02 V to about −1.4 V relative to the second electrode. The negative electrical charge may be pulsed, thereby effecting incremental release of the nucleotide The nucleotides may be in a nucleotide and lipid complex, and the lipid may be a liposome. Similarly, the nucleotide may be thiolated. The nucleotide may be a single-stranded DNA, double-stranded DNA, RNA or other nucleic acid, and may also be an antisense nucleotide.

Also provided is a method for transporting nucleotides across tissue, in which nucleotides to be released are adsorbed on a first electrode. A second and third electrode are provided, and the second and third electrodes, together with the first electrode, are positioned in proximity to a region of tissue in an acqueous media in which the nucleotide is to be released. The tissue can include cells and cell membranes, and in the case of cells may be a monolayer or multiple layer of cells. A negative electrical charge is provided to the first electrode relative to the second electrode, and thereafter at least one electrical pulse is applied to the third electrode of sufficient voltage and duration to cause electroporation in the region of the tissue. In this way, the release of the nucleotide is proportional to the relative electrical charge difference and length of persistence of the charge difference and electroporation is related to the voltage and duration of the electrical pulse, so that the nucleotides are released and transported across the tissue. In the method, the adsorbing can include application of a positive potential to the first electrode to facilitate adsorption. The negative electrical charge applied to the first electrode relative to the second electrode may be a potential difference of from about −0.02 V to about −1.4 V. In this method, the negative electrical charge to the first electrode can be pulsed, thereby effecting incremental release of the nucleotide. Further, the electrical pulse to the third electrode, which provides for electroporation, may also be pulsed, and may further be pulsed in synchronicity with the negative electrical charge pulse.

In this method also the nucleotide may be thiolated, and may be a single-stranded DNA, double-stranded DNA RNA or other nucleic acid. The nucleotide may also be an antisense nucleotide.

The invention further includes an apparatus for controlled nucleotide release, the apparatus including a first electrode with a nucleotide adsorbed onto at least a portion of the surface, a second electrode, and a first power supply connected to the first and second electrode, providing a selectable positive or negative potential difference to the first electrode relative to the second electrode. In another embodiment, the apparatus can further include a third electrode and a second power supply connected to the second and third electrode, providing a selectable voltage output. In this apparatus, the first power supply provides a positive to negative potential difference to the first electrode relative to the second electrode from about at least +0.5 V to about at least −1.4 V. The apparatus can also include a first pulse generator connected to the first power supply, capable of providing defined pulses of positive or negative potential difference to the first electrode relative to the second electrode. In the apparatus, it is preferred that the selectable voltage output of the second power supply is sufficient to cause electroporation of tissue which is placed in proximity to the second and third electrodes. The apparatus can also include a second pulse generator connected to the second power supply, and capable of providing defined pulses of the selectable voltage output.

In this apparatus, the nucleotides may be in a nucleotide and lipid complex, and the lipid may be a liposome. Similarly, the nucleotide may be thiolated. The nucleotide may be a single-stranded DNA, double-stranded DNA, RNA or other nucleic acid, and may also be an antisense nucleotide.

A primary object of the present invention is to provide a means for controlled and specific release of DNA and other nucleic acids within an aqueous environment, including within an organism or within cell culture media.

Another object of the present invention is to provide an apparatus and means for electrochemical immobilization of DNA and other nucleic acids on an electrode, and subsequent potential-controlled electrochemical release of the DNA or other nucleic acids from the electrode.

Another object of the present invention is to provide a non-viral method for delivery of DNA and other nucleic acids in close proximity to target cells, and subsequent release in conjunction with means for enhancing introduction of the DNA or other nucleic acids into the cell.

Another object of the present invention is to provide a two- or three-electrode system, whereby the amount and rate of release of immobilized DNA or other nucleic acids can be manipulated by electrical potential control.

Another object of the present invention is to provide a method for controlled and specific release of DNA and other nucleic acids for use in gene therapy for treatment or prevention of disease.

Another object of the present invention is to provide a means for electrochemical immobilization of either thiolated or non-thiolated DNA and other nucleic acids on an electrode, and subsequent potential-controlled electrochemical release of the thiolated or non-thiolated DNA or other nucleic acids.

Another object of the present invention is to provide a method for the controlled and specific release of complexes formed of lipids or liposomes and DNA or other nucleic acids for use in gene therapy for treatment or prevention of disease.

A primary advantage of the present invention is that it provides a method and apparatus for the controlled and specific release of DNA and other nucleic acids for use in gene therapy for treatment or prevention of disease.

Another advantage of the present invention is that electrochemical release of DNA or other nucleic acids may be combined with electroporation, so that a determined quantity of DNA or other nucleic acids may be released, and the DNA or other nucleic acids thereafter introduced into the target cell.

Another advantage of the present invention is that it permits delivery of DNA or other nucleic acids into a cellular target by means of either simultaneous or sequential electroporation, or by means of lipids or liposome complexes which transit the cellular membrane.

A further advantage of the present invention is that it provides a method for controlled electrochemical release of DNA or other nucleic acids and lipid complexes, which complexes may transit cell membranes and thereafter effect transformation of the target cell.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention.

The drawings are only for the purpose of illustrating a preferred embodiment of the invention and are not to be construed as limiting the invention. In the drawings.

Figure 1:
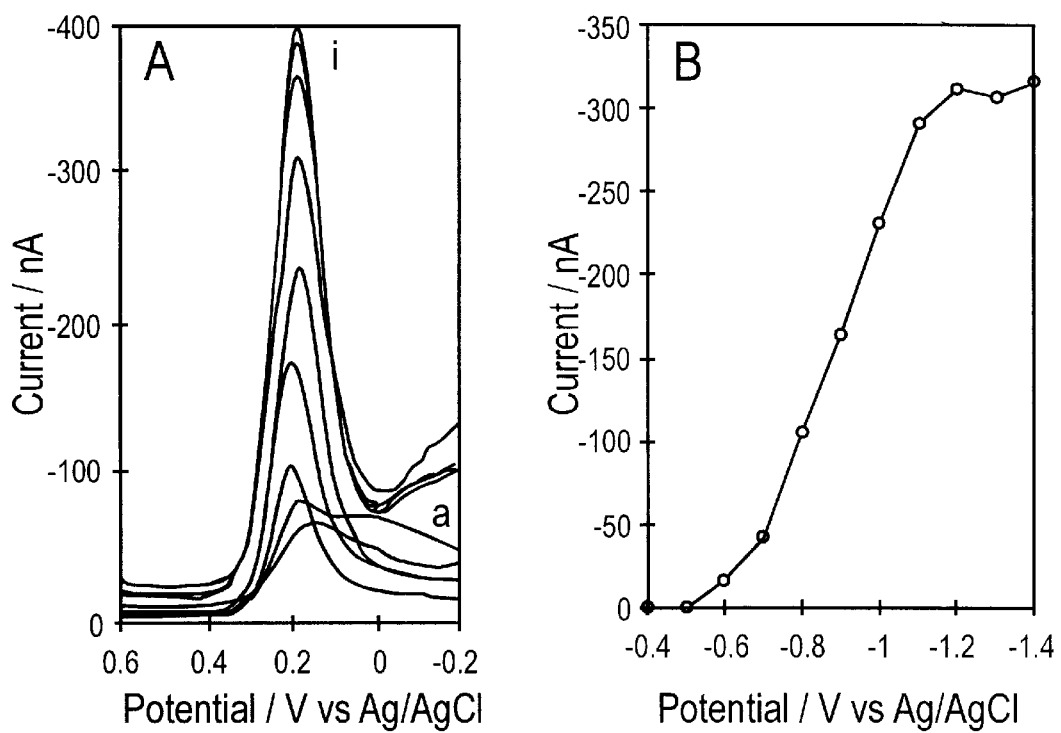
FIG. 1 is a plot of desorption potential in response to potasium ferricyanide at dsDNA-modified carbon paste electrodes, and the resulting peak current versus desorption potential plot.

DESCRIPTION OF THE PREFERRED EMBODIMENTS (BEST MODES FOR CARRYING OUT THE INVENTION)

Using the methods and devices of this invention electrochemical release of nucleotides from electrodes may be effected, such that controlled release of specific quantities of nucleotides is provided. The electrochemical release may be accomplished in conjunction with electroporation or other techniques for increasing cell membrane permeability, such that the nucleic acids may be used to effect gene therapy.

The apparatus of the invention includes art conventional electrodes that may be employed, and particularly glassy carbon electrodes, carbon paste electrodes, metallic electrodes, metal-coated crystal wafer electrodes, and other electrodes. In the preferred embodiment, a three-electrode system is employed, including the nucleotide delivery electrode, such as a carbon paste or gold electrode, a counter electrode, such as a platinum electrode, and a reference electrode, such as an Ag/AgCl electrode. A microelectrode system may be employed, wherein the three electrodes are physically disposed and integrated on a single probe or tip. In another preferred embodiment, a two-electrode system may be employed, including the nucleotide delivery electrode, such as a carbon paste or gold electrode, and a combination counter and reference electrode, which may be platinum, Ag/AgCl, or another metallic electrode.

Where gold or another metallic electrode is employed as the nucleotide delivery electrode, a very small diameter electrode may be employed, of less than 50 µm radius, and preferably of less than 12.5 µm radius. Prior to use, the surface of the metallic electrode is cleaned, and is preferably polished. Any suitable method of polishing may be employed, such as polishing with abrasive paper, alumina or other defined particulate slurries, and the like. In one embodiment, the electrode is first polished with a 600-grit abrasive paper, followed by polishing with 1 µm and 0.05 µm alumina slurries using a napless nylon cloth, resulting in a high mirror finish. The electrode is cleaned by any suitable method, such as by sonication, sonication in water, sonication in ethanol or other solvents, and use of other cleaning solvents and solutions. In one embodiment, the electrode is first sonicated in water and ethanol, and is then sonicated in a solution of 30% hydrogen peroxide and 70% concentrated sulfuric acid, and is then rinsed in water and sonicated in water. Ultra-pure water is preferably employed for all cleaning steps.

In addition to metallic electrodes, other small diameter conductive fibrous materials may be employed as electrodes. In one embodiment, a carbon fiber electrode is employed as the nucleotide delivery electrode, which may be of less than 50 µm radius, and preferably of less than 12.5 µm radius. The electrode is cleaned prior to use by any suitable method, such as by sonication, sonication in water, sonication in ethanol or other solvents, and use of other cleaning solvents and solutions.

Where gold or other metallic or conductive fibrous electrodes are employed as the nucleotide delivery electrode, the nucleotides may be introduced to the surface by immersion of the electrode in a solution containing the nucleotide. For non-thiolated nucleotides, the electrodes may be immersed in a solution containing about 1,000 mg/L of nucleotide in a suitable buffering system, such as 0.1 M Tris-HCl and 10 mM EDTA. Immersion is for a suitable period to introduce a sufficient quantity of nucleotide; in one embodiment, the electrode is immersed in a solution containing 1,000 mg/L of nucleotide, 0.1 M Tris-HCl and 10 mM EDTA for a period of 18 hours at a temperature of 4° C. The concentration of nucleotide, length of incubation, temperature of incubation and buffer solution composition may all be determined empirically, using the methods and examples set out herein. It is to be understood that a wide range of concentrations, buffers, incubation times, incubation temperatures and the like may be employed, yielding substantially similar results. Following introduction of the nucleotides, the electrode may be rinsed using water, and allowed to dry. The result is a surface-confined nucleotide layer on the electrode.

Thiolated nucleotides may also be employed in this invention. Any method of thiolation that results in a reactive sulfur complexed or linked to the nucleotide may be employed. In one method, sonicated nucleotide, in a concentration of about around 6,000 mg/L, is allowed to react with 2-hydroxyethyidisulfide (HEDS, 2.3 mg) in the presence of 1-cyclohexyl-3-(2-morpholinethyl)-carbodiimidemetho-p-toluenesulfonate (0.2 g) in 0.2 mL of 0.04 M MES buffer (pH 6.0) for 24 hours at 25° C. The resulting nucleotide with a phosphodiester linkage between the terminal monophosphate ends of the nucleotide and the hydroxyl group of HEDS is recovered by conventional means, such as column chromatography, with detection by UV spectroscopy, gel electrophoresis, HPLC and the like. Other means of the thiolation of nucleotides may also be employed. The thiolated nucleotide may be introduced to the surface of gold or other metallic electrodes by immersion of the electrode in a solution containing the thiolated nucleotide. For thiolated nucleotides, the electrodes may be immersed in a solution containing about 500 mg/L of thiolated nucleotide in a suitable buffering system, such as 50 mM NaCl and 5 mM phosphate buffer at pH 7.0. Immersion is for a suitable period to adsorb a sufficient quantity of nucleotide onto the surface of the electrode; in one embodiment, the electrode is immersed in a solution containing 500 mg/L of thiolated nucleotide in a 50 mM NaCl and 5 mM phosphate buffer for a period of 48 hours at a temperature of 4° C. The concentration of thiolated nucleotide, length of incubation, temperature of incubation and buffer solution composition may all be determined empirically, using the methods and examples set out herein. It is to be understood that a wide range of concentrations, buffers, incubation times, incubation temperatures and the like may be employed, yielding substantially similar results. Following introduction of the thiolated nucleotide, the electrode may be rinsed using a phosphate buffer solution and water and allowed to dry. The result is a surface-confined thiolated-nucleotide layer on the electrode.

With metallic electrodes, it is also possible and contemplated that electrostatic adsorption may be facilitated by applying a positive charge or potential to the electrode while it is immersed in a suitable solvent containing the nucleotide to be adsorbed. In one embodiment, the nucleotide is adsorbed onto the surface of a gold electrode by immersing the electrode into a solution containing the nucleotide, and applying a potential of +0.5 V for 5 minutes. The electrode may thereafter be washed, using water or other suitable buffers, and allowed to dry prior to use.

Carbon paste electrodes, including carbon paste microelectrodes, may also be employed as the nucleotide delivery electrode. The electrodes may be made from graphite powder and mineral oil, and packed into a suitable tube or other hollow receptacle. Any of a wide variety of carbonaceous materials may be employed for the carbon paste electrode, including reticulated carbon. One end of the carbon paste electrode is attached to a suitable wire, such as a copper wire, to provide an electrical contact. Fresh surfaces of the electrode may be obtained by cuffing, polishing or the like. The interior diameter of the tube may be any suitable diameter, ranging from about 200 $\mu$m interior diameter or smaller to about 2 mm interior diameter or larger.

With carbonaceous nucleotide delivery electrodes, the nucleotide may be immobilized onto the surface by means of electrostatic adsorption. In one method, the nucleotide may be immobilized onto the surface by immersing the electrode in a stirred acetate buffer solution at about pH 5.0, containing about 30 ppm nucleotide, and applying a potential of +0.5 V for 5 minutes. The electrode may thereafter be washed, using water or other suitable buffers, and allowed to dry prior to use. Alternatively, the carbonaceous electrode may by immersed in a solution containing the nucleotide and allowed to incubate for a suitable period, up to and including 48 hours or more, without applying any potential, such that the nucleotide is adsorbed onto the electrode.

Any of a variety of nucleotides may be employed with the nucleotide delivery electrodes of this invention. The nucleotides can range from oligonucleotides, such as 25-mer or shorter ssDNA, to dsDNA of greater than 350 base pair length. The nucleotides may be used for transfection of cells, as in treatment of cancer or any of a wide variety of diseases of genetic origin. Anti-sense nucleotides may have particular application for medical applications.

Further, the nucleotides may be altered in any desired method, such as by thiolation or by conjugation or complexation to any of a wide variety of substances. In one preferred embodiment, the nucleotides include a carrier, which may be a protein, polypeptide, polysaccharide, phospholipid, cationic lipid, glycoprotein, lipoprotein or lipopolyamine. In one embodiment, the carrier is or can be cationized by introducing positively charged side groups, with the bonding between the carrier and the nucleotide being effected by adsorptive or covalent bonding. A wide variety of carriers for nucleotides are known in the art, and are described in U.S. Pat. Nos. 5,916,803, 5,908,635 and 5,892,071, among others, incorporated herein by reference. The carriers that may be preferably employed within the context of the present invention include liposomes, cationic liposomes that are prepared using cationic lipids such as stearyl amines in a mixture with neutral phospholipids, other neutral phospholipids compositions, and the like. Other cationic polypeptides and proteins, such as polylysine, protamine sulfates, polyarginine and the like, may also be employed as carriers, as may cationic amphiphilic lipopolyamines, cationic polysaccharides or cationic organic polymers. These may each be complexed with the nucleotide by any means known in the art. One form of liposome that may be employed is available under the trademark LIPOFECTIN (Gibco BRL, Gaithersburg, Md.). LIPOFECTIN liposomes and nucleotide complexes are understood to form through the electrostatic interaction of the negative charges of the nucleotide and the positive charges at the surface of the cationic liposomes. The resulting complex fuses with cells and facilitates the delivery of functional genetic material into cells. A wide variety of cationic liposomes are known in the art, and may be obtained from any of a wide variety of suppliers or may be made by methods of synthesis known in the art.

The nucleotide or nucleotide and carrier complex may also include a fusion protein employed to facilitate penetration of the nucleotide into the cytoplasm of the desired target cell. A number of fusion proteins of this nature are known, especially from viral sources.

The specific gene that is to be introduced by the nucleotide can be in the form of a nucleic acid containing the desired gene, and may further include appropriate regulatory regions such as promoters, enhancers and so on. In a preferred embodiment, the nucleotide includes a gene that is to be introduced in the form of a plasmid. The regulatory regions added to the desired gene may include viral promoter sequences or enhancer sequences utilized to amplify or extend expression of the gene.

The various components forming the nucleotide and carrier complex may be bonded together by any means known in the art, including covalent bonds, ionic interaction, and adsorption forces. Further, for a complex that includes more than two components, more than one form of bonding may be employed. Thus, for example, regulatory regions or other components may be added to DNA by covalent bonds, and the resulting DNA complex may be used to form a liposome and DNA complex by electrostatic interaction.

Any of the various complexes of nucleotides and carriers may be employed in this invention. In a preferred embodiment of this invention, a DNA and lipid complex is utilized, such that the complex results in increased cellular permeability. In one embodiment, a DNA and liposome complex may be employed. The various complexes may be used with any of the nucleotide delivery electrodes of this invention.

The surface of the nucleotide delivery electrodes of this invention may be modified in order to increase the surface area, and thereby increase the surface loading of nucleotides. For carbonaceous nucleotide delivery electrodes, granulated or microporous compositions may be employed. It is also possible, with metallic or carbonaceous nucleotide delivery electrodes, to employ multiple layer electrodes, or electrodes with rough, recessed, reticulated, porous or other surfaces, or made utilizing a foam-like or cell-like structure.

With any of the nucleotide delivery electrodes of this invention, desorption of the surface-confined layer of nucleotides or nucleotide complexes may be effected by potential control. This may be done in any suitable aqueous media, such as a phosphate buffer solution. The media may be specifically employed such that it supports cell life, and may include any of a variety of stimulatory agents, supplements, antibiotics, minerals and the like. The media may be at any pH that supports cell life for the cell to be transfected, and may preferably be at physiologic pH for the organism. In a preferred embodiment, a 0.05 M phosphate buffer solution is employed, at pH 7.4. The desired and effective potential control may be determined empirically, and may be varied to effect the rate of desorption of the nucleotide or nucleotide complex. For carbonaceous nucleotide delivery electrodes, a selected potential of approximately −1.2 V may be employed for a period of about 2 minutes, which will effect desorption of all or substantially all of the nucleotide or nucleotide complex. For desorption of controlled amount, a decreased potential, such as from about −0.4 V to about −1.2 V may be employed, and similarly decreased periods may be employed. Thus, for example, sequential desorption may be obtained by essentially pulsing the electrode, for periods of a few seconds or less, followed by periods without any effective negative potential. For metallic nucleotide delivery electrodes, a similar method may be employed, such as desorption by a potential of about −1.0 V to about −1.3 V for a period sufficient to release the nucleotide or nucleotide complex, generally on the order of less than 10 minutes. As with the carbonaceous electrode, the potential control and length of application of potential may be varied to select the rate of desorption of the nucleotide or nucleotide complex.

Prior to effecting desorption, it is desirable to stabilize the three-electrode system by the application of a positive potential, on the order of at least about +0.4 V. Thereafter, the potential may be modulated as desired to effect desorption.

Similar methods may be employed with a two-electrode system, with a positive potential applied to the nucleotide delivery electrode relative to the combination counter and reference electrode, and thereafter the potential modulated as desired to effect desorption. In one embodiment, the potential is modulated to at least −1.0 V for intermittent periods of from 1 to 10 seconds, to effect controlled release over a determined period of time.

It is also possible and contemplated that desorption may be effected and measured in terms of applied current, such that a negative current is applied to the nucleotide delivery electrode. The rate of flow of charge thereby determines the rate of desorption of the nucleotide, which rate may be modulated, pulsed and otherwise altered to effect controlled desorption.

The apparatus of this invention further includes the various components required for application of the desired current to the electrodes, control of applied current and potential, measurement of current and potential, electrode cells and the like. The apparatus thus includes a power supply, and may include an electrochemical analyzer, modular electrochemical system or other like.

In this application and the claims, "ssDNA" refers to single-stranded DNA, and "dsDNA" refers to double-stranded DNA. "DNA" refers to deoxyribose nucleic acid. "RNA" refers to ribonucleic acid. It is to be understood that the methods and apparatus of this invention may be used with any nucleic acid or nucleotide, including single or double stranded molecules, and including both natural and manufactured sequences, including sense and anti-sense compositions. The term "nucleotide" includes each of the foregoing.

Industrial Applicability

The methods and apparatus of this invention may be used in conjunction with electroporation techniques for increase cell membrane permeability, such as those taught in U.S. Pat. Nos. 5,019,034, 5,749,847, 5,869,326, 5,993,434, 6,014,584, 4,081,340 and 5,964,726, the teachings and disclosures of which are incorporated by reference. In one embodiment, the three-electrode system of this invention can be combined with a two-electrode electroporation apparatus, such as in a microprobe wherein the tip includes five distinct electrodes, three for use in release of DNA by the methods and apparatus of this invention, and two for use in electroporation to increase cell membrane permeability. In this way a single multi-electrode probe may be utilized to transport DNA, to effect controlled release of DNA, and to increase cellular permeability to facilitate transfer of the DNA across the cell membrane for subsequent transfection, resulting in a transformed cell. It is also possible and contemplated that a four-electrode system is employed, including a two-electrode system for electrochemical release of nucleotides of this invention and a two-electrode electroporation apparatus.

In another embodiment, the three-electrode apparatus of this invention is employed, with two of the three electrodes, such as the counter electrode, as for example a platinum wire counter electrode, and the reference electrode, as for example an Ag/AgCl reference electrode, also employed for use in electroporation. In this embodiment, the apparatus may be so configured that release of the DNA is first effected, followed by electroporation, or alternatively, the apparatus may be so configured such that a portion of the DNA is release, followed by one or more electroporation pulses, followed by release of a second portion of the DNA, followed by one or more subsequent electroporation pulses, and so forth.

In those embodiments employing electroporation, whether through use of independent electrodes for electroporation, or through use of one or more of the two or three electrodes of the apparatus of this invention, the apparatus may further include those elements required for electroporation, including pulse delivery of low and high voltage, such as one or more power supplies, switches, controllers, energy storage reservoirs and the like.

The methods and apparatus of this invention may also be used in conjunction with any nucleotide complex, including complexes intended to facilitate DNA passage through cell membranes. Thus the nucleotide complex may include targeting components, liposomes, peptides and various other substances or carriers. When used with liposomes or other targeting methods and elements, electroporation is not required to effect transfection of the target cell.

The methods and apparatus of this invention may also be employed for other uses wherein controlled, sustained or specific release of DNA or other nucleotides is desired. One such application is as an electrode in scanning probe microscopy ("SPM"). In SPM, as in for example scanning tunneling microscopes or atomic force microscopes, a probe is employed, and materials adsorbed onto the probe may be used in microscopy studies. Thus the methods and apparatus of this invention can be employed as an SPM probe tip, allowing for controlled release of DNA or other nucleotides as desired. Other applications include localized immobilization of DNA or other nucleotides for use on gene chips, for "lab-on-a-chip" devices, for genoelectronic devices, composite materials, bioactive interfaces, other "on-chip" devices and biomaterial-based devices, for use in genetic analysis, diagnostic applications, computational applications and the like.

The invention is further illustrated by the following non-limiting examples.

EXAMPLE 1
Fabrication of the Carbon Paste Electrodes

Carbon paste was prepared by thoroughly hand-mixing graphite powder and mineral oil with a graphite/oil mass ratio of 70/30, for 20 minutes. A portion of the resulting paste was packed into the end of a 5-cm long Teflon tube (280 $\mu$m i.d., 600 $\mu$m o.d). The paste filled the Up to a height of about 5 mm. A copper wire (0.2 mm diameter), introduced from the opposite end, provided the electrical contact. The resistance of the resulting microelectrode was about 400Ω. Fresh carbon surfaces were obtained by cutting the tip of the electrode with a sharp surgical knife to allow multiple applications. Conventional carbon electrodes were prepared by packing the paste into a Teflon electrode body (2 mm diameter) and polishing the surface on a weighing paper prior to use.

EXAMPLE 2
Carbon Paste Three Electrode Apparatus

A three-electrode system consisted of a carbon paste working electrode (0.28 or 2.0 mm diameter), an Ag/AgCl (3M NaCl) reference electrode (Model RE-1, BAS) and a platinum wire counter electrode. The electrochemical glass cells (4 ml vials) were cleaned with diluted nitric acid (1:4), rinsed thoroughly with autoclaved water and dried prior to use. All pipette tips and distilled water used were sterilized by autoclaving for 30 minutes.

Square wave voltammetric ("SWV") measurements were performed using a modular electrochemical system Autolab (Eco Chemie, Utrecht, The Netherlands), equipped with PSTAT10 and driven by GPES software (Eco Chemie). Chronopotentiometric stripping measurements were performed with a TraceLab Potentiometric Stripping Unit (PSU20, Radiometer, Denmark) connected to a personal computer and controlled by TAP2 software (Radiometer). Energy Dispersive X-ray Microanalysis ("EDX") data were obtained with a Hitachi S-3200N Scanning Electron Microscope (Hitachi, Japan), equipped with Kevex-EDX system (Kevex Instruments, Valencia, Calif.).

EXAMPLE 3
Reagents Used with Carbon Paste Electrode

Calf thymus dsDNA and ssDNA, stock solutions of Tris-EDTA buffer (1 M Tris-HCl, 0.1M EDTA), sodium acetate buffer, and potassium ferricyanide were used as received. Stock solutions (1000 mg/L (ppm)) of dsDNA or ssDNA were prepared in diluted Tris-EDTA buffer (10 mM Tris-HCl, 1 mM EDTA). Acetate buffer (0.2M, pH 5.0) or potassium chloride (0.1M KCl) served as supporting electrolytes. All other reagents were analytically pure and used as received. The water used for preparing the solutions was autoclaved for 30 minutes prior to use.

EXAMPLE 4
DNA Immobilization and Resorption on Carbon Paste Electrodes

Electrodes of Example 1 were electrochemically pretreated in 0.2 M acetate buffer (pH 5.0) by applying first a potential of +1.7 V for 1 minute and then −1.0V for 1 minutes, using a two potential step amperometric mode. The nucleic acids were immobilized onto the pretreated surfaces by immersing the electrode in a stirred acetate buffer (pH 5.0) solution, containing 30 ppm ssDNA or dsDNA, and applying a potential of +0.5 V for 5 minutes.

The desorption of surface-confined DNA layer was conducted in a quiescent phosphate buffer solution (0.05 M, pH 7.4) by applying the selected potential (usually −1.2 V) for different periods (commonly 2 minutes). The electrode was then rinsed with water and transferred into a proper solution for subsequent characterization. The desorption potential has a profound effect upon the ability to deliver the genetic material. FIG. 1 assesses the influence of the desorption potential upon the voltammetric response of a ferricyanide marker. No change in the marker response was observed for potentials lower than 0.50V. The ferricyanide peak increased slowly for potentials ranging between −0.5 V and −0.7 V, more rapidly between −0.7 V and −1.1 V, and more slowly thereafter.

Figure 2:
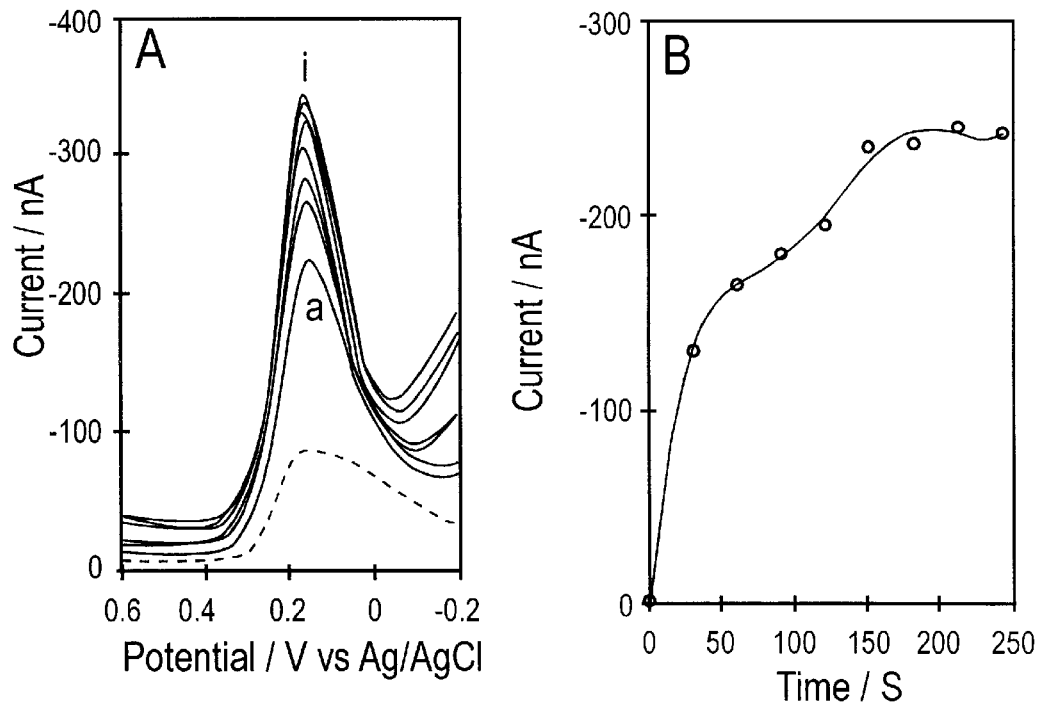
FIG. 2A is a plot of desorption time in response to potasium ferricyanide at dsDNA-modified carbon paste electrodes.
FIG. 2B is the resulting peak current versus desorption time plot.

FIG. 2 displays the effect of the desorption time upon ferricyanide peak current. The response increases rapidly the desorption time at first up to 60 seconds, then more slowly (between 60 and 180 seconds), and leveled off at longer periods. Such profile indicates the ability to release small amounts of nucleic acids at specific times through repetitive potential pulses. A slower release over extended periods may be accomplished through the use of lower desorption potentials.

Figure 3:
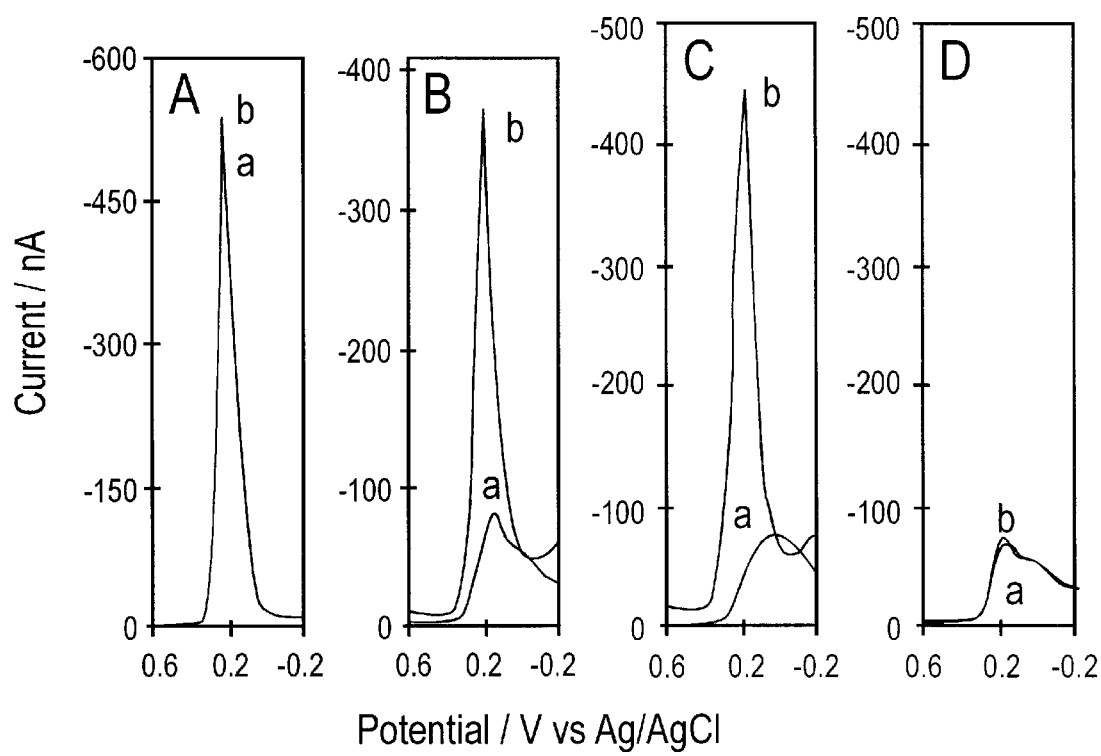
FIGS. 3A through 3D are voltammograms of DNA-modified and bare carbon paste electrodes.

EXAMPLE 5
Square Wave Voltammetric (SWV) Blocking Experiments with Carbon Paste Electrodes SWV monitoring of the DNA desorption efficiency was performed with a ferricyanide redox marker using the apparatus and reagents of Examples 2 and 3. The carbon electrode of Example 1 was immersed in a quiescent 0.1M KCl solution, containing $1\times10^{-3}$ M of potassium ferricyanide marker. The SWV scan, between +0.6 and −0.2V, used a frequency of 25, potential step of 25 mV, and an amplitude of 20 mV. Votammograms were recorded at the DNA-coated electrode before or after the DNA desorption. FIG. 3 (B and C) displays voltammograms for the ferricyanide redox marker following the adsorption (a) and desorption (b) of ssDNA and dsDNA, respectively. Also shown as control experiments are analogous voltammograms at the uncoated surface (A) and at the dsDNA-modified electrode without applying the desorption potential (D). At the bare electrode, the marker signal remained nearly identical after 2 minutes at a desorption potential of 1.2 V, indicating that such potential has negligible effect upon the electrochemical behavior of ferricyanide (A, a vs. b). The adsorptive immobilization of both ssDNA and dsDNA resulted in substantial suppression, approximately 80%, of the marker response (a, B and C), reflecting the high surface coverage. Transferring these nucleic-acid modified electrodes to a phosphate-buffer blank solution, and applying the desorption potential of −1.2 V for 2 minutes, resulted in restoration of the ferricyanide signal, to values similar to those of the uncoated electrode [b (B and C vs. A)]. Such restoration reflected the release of the DNA layers from the carbon surface under physiological pH. When the same experiment was repeated using open-circuit conditions instead of −1.2 V, the suppressed ferricyanide peak did not increase (a vs. b, D), indicating no effect upon the adsorbed dsDNA layer. No suppression of the ferricyanide peak was observed in the presence of a large excess of the Tris-HCl and EDTA constituents of the DNA solution.

EXAMPLE 6
Potentiometric Stripping Analysis with Carbon Paste Electrodes

Figure 4:
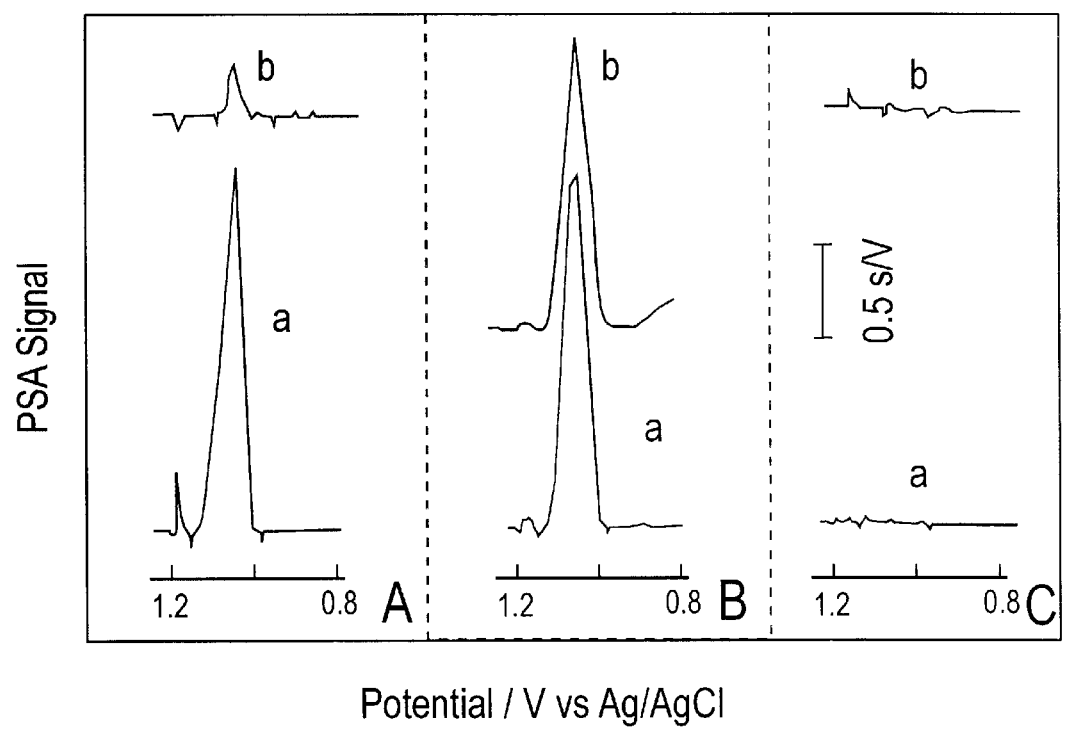
FIGS. 4A through 4C are chronopotentiometric stripping curves at a dsDNA-modified carbon paste electrode at −1.20 volts and open circuit, and a bare carbon paste electrode, respectively.

Potentiometric stripping probing of the surface-confined nucleic acids was performed in one ml of acetate buffer solution (0.2 M, pH 5.0) using the electrodes of Example 1, apparatus of Example 2 and reagents of Example 3. This was accomplished by applying a constant oxidative current of 5 $\mu$A at the DNA-modified electrode before and after desorption of the attached nucleic acid and monitoring changes of the oxidation peak of the guanine moiety. The curve data were filtered and baseline corrected. Each "immobilization-desorption-stripping" cycle employed a new electrode surface. The medium-exchange/chronopotentiometric protocol provides a direct quantitation of the surface-confined DNA by measurement of oxidation of the guanine moiety. FIG. 4A displays representative chronopotentiograms for the dsDNA-modified carbon-paste electrode before (a) and after (b) applying a potential of −1.2 V for 2 minutes. The well-defined guanine response observed after the DNA accumulation (FIG. 4A(a)) decreased dramatically, approximately 90%, after 2 minutes at −1.2 V, reflecting removal of DNA. Only a very small change, approximately 5%, in the response of the surface-confined DNA was observed when the same experiment was repeated by holding the electrode for 2 minutes at open circuit instead of −1.2 V (FIG. 4B (a vs. b)). No response was observed in analogous medium-exchange/chronopotentiometric experiments utilizing the bare carbon-paste microelectrode (FIG. 4C).

EXAMPLE 7
EDX Characterization with Carbon Paste Microelectrodes

Figure 5:
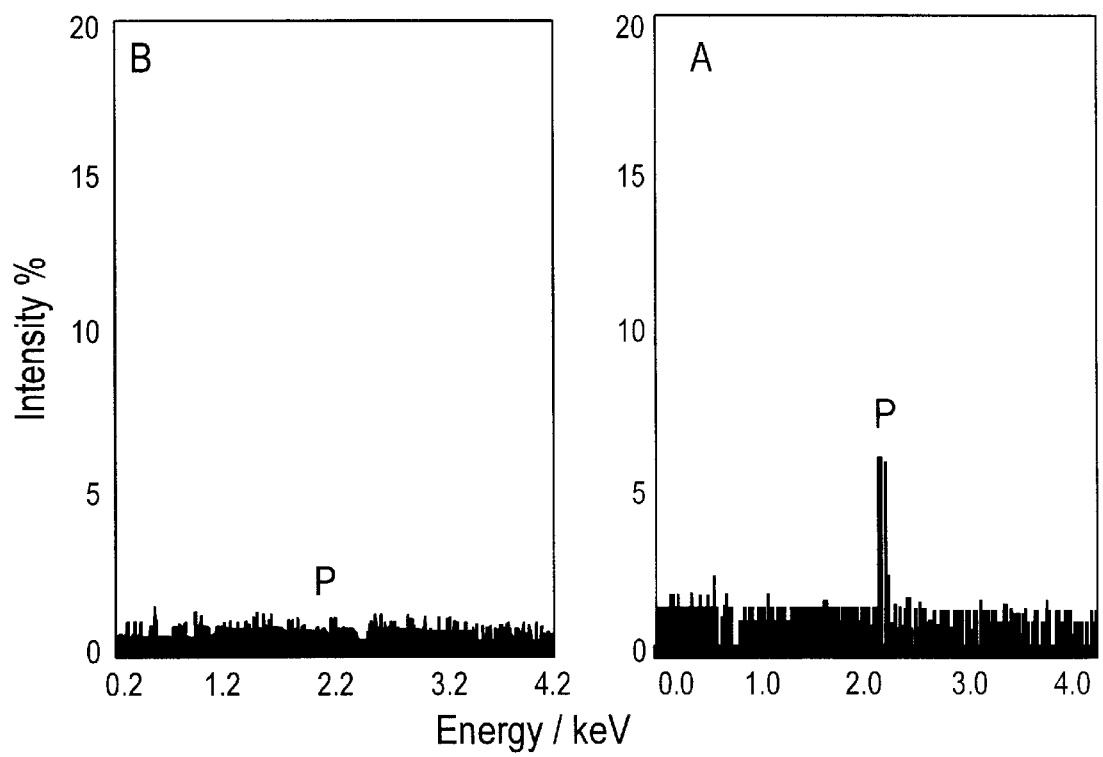
FIG. 5 depict EDX spectra before and after applying a desorption potential of 1.2 volts for two minutes in 0.05 M phosphate buffer at pH 7.4.

EDX spectra were obtained at DNA coated carbon paste microelectrodes of Example 1 using the apparatus of Example 2 before and after the electrochemically-induced desorption using point-analysis method at magnification ×6000, using accelerate voltage of 20 kV, and a sample-detector distance of 20 mm. Before mounting and inserting the samples into the vacuum chamber, they were thoroughly rinsed with water and then dried at room temperature. Low vacuum ($10^{-3}$ torr) was selected to minimize system contamination due to the mineral-oil carbon samples. Both the nitrogen (N) and phosphorous (P) peaks can be used for confirming the presence of DNA on the surface. Due to the proximity of the N peak (at 0.392 KeV) to the large carbon signal (at 0.277 KeV), the P peak (at 2.013 KeV), associated with the sugar-phosphate backbone of the DNA, was employed. FIG. 5 displays EDX spectra of the dsDNA-modified carbon-paste surface before (A) and after (B) applying the desorption potential of −1.2 V for 2 minutes. Over 80% diminution of the P peak was observed after applying the potential, indicating the removal of most of the accumulated DNA layer.

EXAMPLE 8
Preparation of Gold Ultramicroelectrodes

A 1-cm long individual gold fiber with a radius of either 12.5 $\mu$m or 50 $\mu$m was placed at the end of a glass pipette tip (1.5 mm O.D., 1 mm I.D.). A coil of resistively heated Nichrome wire on a vertical pipette puller was used to melt the glass around wire. High-purity silver conducting paint was employed to make electrical contact to a copper wire that was used as the electrical connection. Each electrode was polished first with a 600-grit abrasive paper, followed by polishing with 1 $\mu$m and 0.05 $\mu$m alumina slurries (on napless nylon cloths) to a mirror finish. The surface of the electrodes was cleaned by sonication in both ethanol and water for 10 minutes and then with a Piranha (30% hydrogen peroxide/70% concentrated sulfuric acid) solution for an additional 2 minutes. Subsequently, the electrodes were carefully rinsed with water and sonicated for an additional 10 minutes in water. The electrodes were repolished with 0.05 $\mu$m alumina slurry and washed prior to each experiment. Optical characterization of the resulting electrodes (at 4000× magnification) revealed defined disk shapes and smoothed surfaces. Cyclic voltammetric evaluation of newly prepared microelectrodes using ferricyanide demonstrated a very good agreement with the theoretical current value.

EXAMPLE 9
Preparation of Apparatus for Use with Thiolated DNA

Electrochemical quartz microbalance ("EQCM") experiments employed a Maxtek Plating Monitor (Model PM-740, Maxtek Inc., Torrance, Calif.), interfaced to an IBM personal computer and to a CH Instruments 620 electrochemical analyzer (CH Instruments, Cordova, Tenn.). This apparatus drove the quartz crystal at its resonance frequency while serving to display and record the value of this frequency. The QCM cell, supplied by Universal Sensors Inc. (Metairie, La.), was set up in static operation mode. It was connected to the frequency monitor, as well as to the electrochemical analyzer, providing in-situ frequency monitoring under potential control. AT-cut quartz crystals with a fundamental resonance frequency ($F_o$) of 5 MHz were provided by International Crystal Manufacturing Co. (Oklahoma City, Okla.). The crystal wafers were loaded with gold-coated electrodes (area: 41 mm$^2$×2; average gold thickness, 100 nm), formed by thermal evaporation of gold to a pre-deposited chromium underlayer on quartz matrix. An HC-48 holder (ICM, Oklahoma City, Okla.) provided the contacts of the oscillating crystals to both the oscillating circuit and electrochemical closed circuit. A platinum wire counter electrode and an Ag/AgCl (3 M NaCl) reference electrode (Model RE-1, BAS) were used for the three-electrode electrochemical set-up. Experiments were conducted by fully immersing the bare/modified crystal into a phosphate buffer solution (0.05 M, pH 7.40).

High resolution X-ray photoelectron spectroscopy ("XPS") experiments were performed with AKIS-HSi XPS Spectrometer (Kratos Analytical Co., U.K.). The unit was equipped with a hemispherical analyzer (with a pass energy of 40 eV and resolution of 0.1 eV), toroidal monochromator, and multichannel detector. A monochromated Al-anode (Al K$\alpha$ radiation line: 1486.6 eV) was used as the X-ray source. Photoelectrons were collected at a 90° take-off angle, with acquisition times shorter than 10 minutes. The sampling area was 500 $\mu$m×500 $\mu$m. The base pressure of the XPS chamber during measurements was below 1×10$^{-10}$ Torr.

Voltammetric and chronoamperometric experiments were performed using the Autolab modular electrochemical system (Eco Chemie, Utrecht, The Netherlands) equipped with PGSTAT 10 and driven by GPES software (Eco Chemie). A gold disk microelectrode (of 12.5 or 50 μm radius) was used as working electrode. The reference and counter electrodes were the same as described above.

EXAMPLE 10
Preparation of Thiolated dsDNA

The synthesis of the thiolated dsDNA was based on the protocol of Maeda et al. (Maeda, M.; Mitsuhashi, Y.; Nakano, K.; Tagaki, M. *Anal. Sciences* 1992, 8, 83.) Briefly, 5 miligrams of calf thymus dsDNA were dissolved in 5.00 mL of a 0.015 M NaCl/0.0015 M sodium citrate solution (pH 6.6) and sonicated. The sonicated DNA was precipitated by adding 10.00 mL of ice-cold 95% ethanol, centrifuged at 14000 rpm for 10 minutes and redissolved in 0.2 mL N-morpholinoethane-sulfonic (MES) buffer (0.04M, pH 6.0). After electrophoresis in 0.5% agarose gel in TBE buffer (1×) (10×TBE buffer: 0.89M Tris-HCl+0.89 M boric acid and 0.02 M EDTA), the sonicated DNA showed a broad band centered around 350 bp. Sonicated calf thymus dsDNA was allowed to react with 2-hydroxyethyidisulfide (HEDS, 2.3 mg) in the presence of 1-cyclohexyl-3-(2-morpholinethyl)-carbodiimidemetho-p-toluenesulfonate (0.2 g) in 0.2 mL of 0.04 M MES buffer (pH 6.0) for 24 hours at 25° C. After reacting, a phosphodiester linkage between the terminal monophosphate ends of the DNA and the hydroxyl group of HEDS resulted. The reaction mixture was separated by using a Sephadex G-25 DNA column, eluted with MES buffer (0.04M, pH 6.0), with collected aliquots checked by UV spectroscopy. Those displaying a characteristic peak at 260 nm were checked by gel electrophoresis in 0.5% agarose in TBE buffer. This fraction, which showed a broad band around 350 bp, was used for further work. The final concentration of the thiolated dsDNA in this fraction was 850 mg/L.

EXAMPLE 11
Immobilization of DNA on Gold Disk Microelectrodes

Thiolated DNA-modified gold disk microelectrodes were prepared by self-assembly of the corresponding thiolated nucleic acids (single-stranded or double-stranded) and alkanethiol (1-octadecanethiol). The surface was modified by immersing the electrodes in 50 mM NaCl/5 mM phosphate buffer (pH 7.0) quiescent solutions containing 500 μg/mL of the 25-mer thiolated-ssDNA or 425 mg/L of the thiolated-dsDNA of Example 10 for a 48 hour period at 4° C. A 1 mM 1-octadecanethiol/ethanol solution was used for preparing the alkanethiol-modified microelectrodes. The modified surfaces were then washed with a phosphate buffer solution (0.05M, pH 7.4) and water and were subsequently allowed to dry.

EXAMPLE 12
Coating with Non-Thiolated Oligonucleotides

Gold microelectrodes as in Example 8 were coated by immersion at 4° C. for sixteen hours in a 1000 mg/L dsDNA or ssDNA solution containing 0.1M Tris-HCl and 10 mM EDTA. The modified surfaces were then washed with water and were allowed to dry. The desorption of the surface-confined DNA layer from the microelectrode was examined in a stirred PBS solution by applying the selected potential for different periods, generally −1.2 V for 10 minutes. The electrodes were then rinsed with water and transferred into a 1 M KCl solution containing 1 mM of the $K_3Fe(CN)_6$ marker for subsequent voltammetric characterization. The square-wave voltammetric scan (from +0.4 to −0.1) was recorded before or after the DNA desorption. All experiments were conducted at room temperature.

EXAMPLE 13
EQCM Measurements with Thiolated Oligonucleotides

Figure 6:
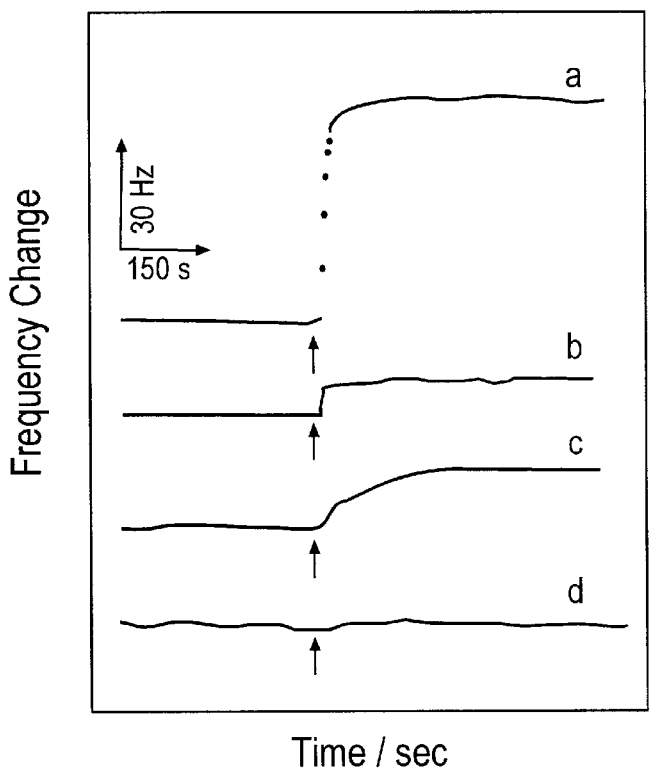
FIG. 6 depicts the time course of frequency change of coated and uncoated crystals upon switching the applied potential.

EQCM was used to study the electrochemically-triggered release of nucleic acids by in-situ monitoring of the mass changes associated with the reductive desorption of the surface layer. The apparatus of Example 9 was used. FIG. 6(a–c) displays typical time courses of the frequency change of different DNA- and alkanethiol-coated crystals (at pH 7.4) upon stepping the potential from 0.0 V to −1.30 V (vs. Ag/AgCl). Also shown (d) is the corresponding frequency-time response of the uncoated (control) crystal. All coated crystals display an increase of their resonance frequency upon the potential step, reflecting the decreased mass associated with the reductive desorption. Both the ssDNA- and 350 bp dsDNA-modified crystals responded very rapidly to the potential step, attaining steady states within 115 and 170 seconds, respectively. A slower change (260 seconds for steady state) was observed at the 1-octadecanethiol-coated crystal. As expected, no frequency change was observed in the control experiment using the unmodified crystal. Steady-state frequency changes of 14.7, 7.1, and 64.4 Hz were observed for the desorbed alkanethiol, ssDNA, and dsDNA, respectively. Such frequency changes correspond to the removal of 106 ng alkanethiol, 51 ng 25 mer ssDNA, and 466 ng of the 350 bp dsDNA (and to surface densities of $9.1 \times 10^{-10}$, $1.3 \times 10^{-11}$, and $4.8 \times 10^{-12}$ mol/cm$^2$, respectively). The steady-state frequency response, and the fact that the frequency did not change further when the experiments of FIGS. 6(a and b) were followed by a second potential step from 0.0 V to −1.30 V, indicate a complete removal of the surface-confined nucleic acids.

Figure 7:
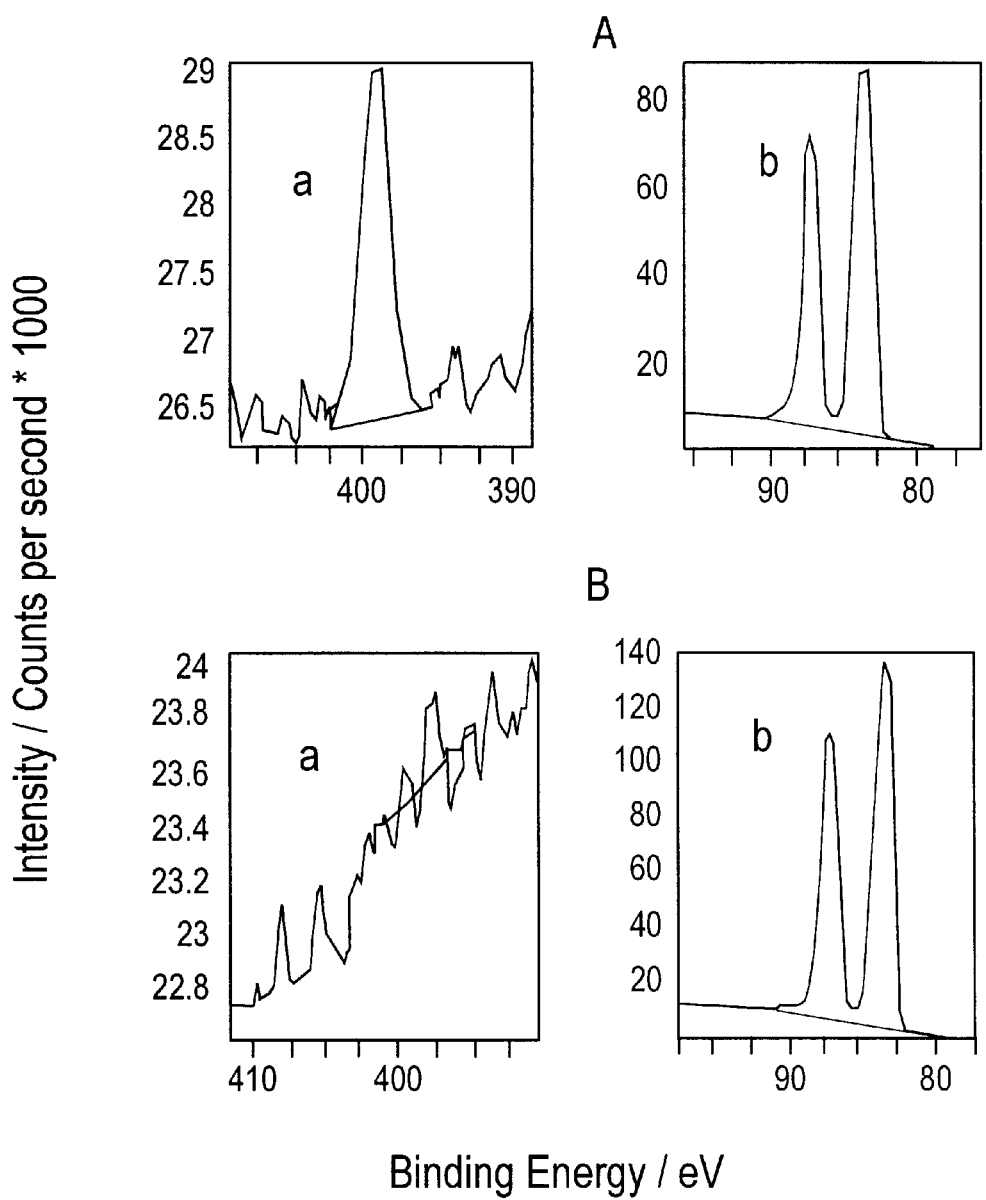
FIG. 7 depicts XPS spectra of ssDNA-coated surface before and after applying desorption potential.
Figure 8:
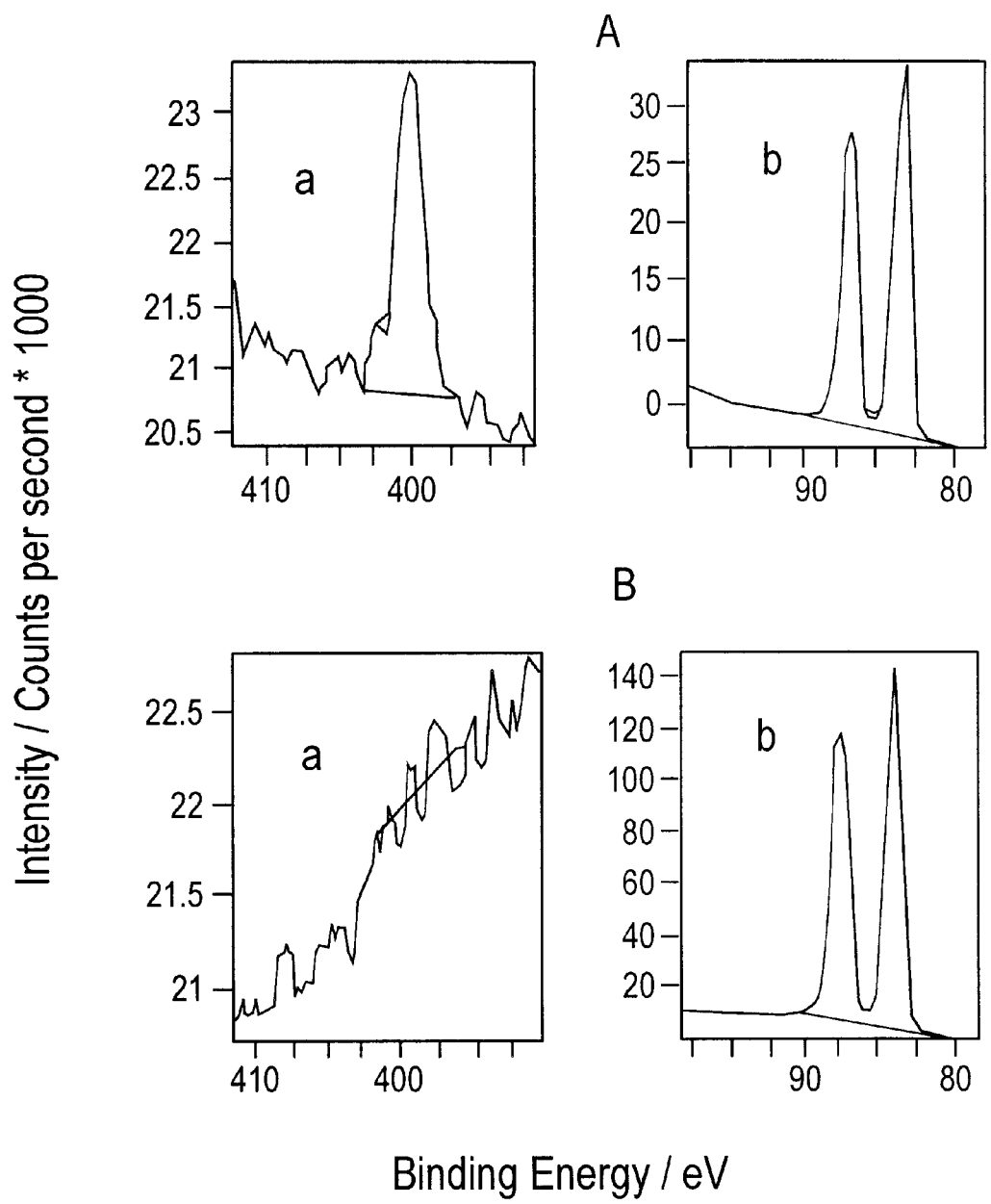
FIG. 8 depicts XPS spectra of dsDNA-coated surface before and after applying desorption potential.

EXAMPLE 14
X-Ray Photoelectron Spectroscopy of Thiolated Oligonucleotide Probes XPS was employed to probe the electrochemical removal of the surface-confined nucleic acids. FIGS. 7 and 8 display XPS spectra of ssDNA- and dsDNA-coated gold surfaces, respectively, before (A) and after (B) applying a potential of −1.30 V for 10 minutes. Both coated electrodes displayed a distinct N 1s peak (at ca. 400 eV; A(a)), characteristic of the nitrogen-containing bases of adsorbed DNA. Essentially no nitrogen peak was observed after holding the electrode at −1.30 V (B(a)), reflecting the removal of the DNA from the surface, A similar XPS profile was obtain ed for an unmodified and bare surface electrode, used as a control (not shown). Changes in the intensity of the Au 4f XPS signals were also used for assessing the reduction desorption of the nucleic acids (FIGS. 7(b) and 8(b)). The areas of these Au 4f peaks at the ssDNA- and dsDNA-coated electrodes were approximately 55% and 25%, respectively, of those observed after 10 minutes at −1.30 V (compare b (A vs. B)). The XPS Au peaks followed desorption of ssDNA and dsDNA (B (b); FIG. 7 vs. 8)). Such peaks were similar to those obtained with the uncoated control surface. Incomplete removal of the sulfur was indicated from the 80% attenuation of the S 2p (at ca. 162 eV) after desorption.

Figure 9:
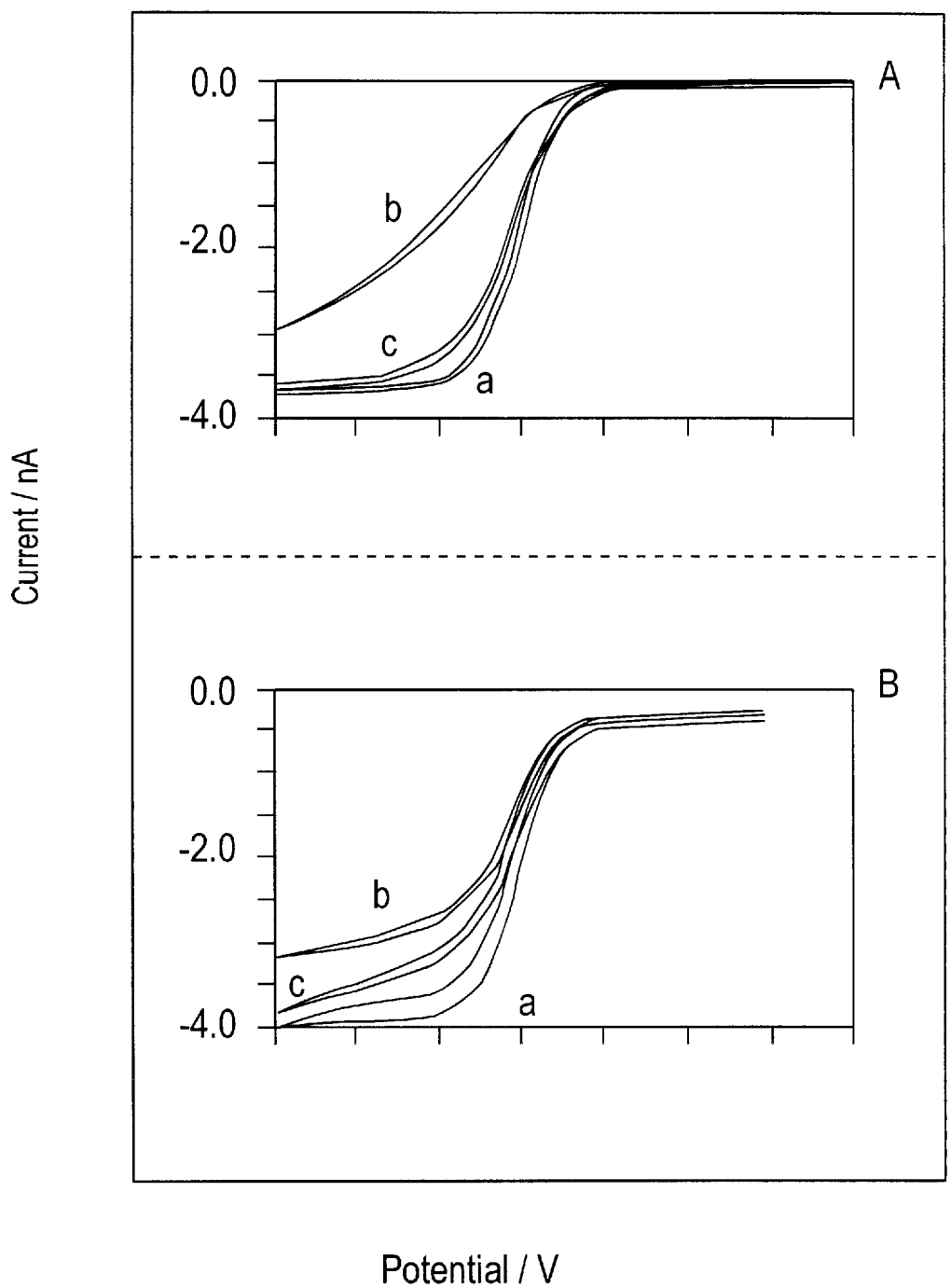
FIG. 9 depicts cyclic voltammograms utilizing gold electrodes.

EXAMPLE 15
Controlled Release of Thiolated Oligonucleotides from Ultramicroelectrodes Gold ultramicroelectrodes were prepared as in Example 8 above. Another set of experiments confirming the controlled release of the genetic material relied on cyclic voltammetry (CV) probing of the barrier properties. FIG. 9 shows typical CVs at 12.5 μm radius microelectrodes before (a) and after (b) the assembly of a thiolated 25-mer oligonucleotide (A) or 350 bp dsDNA (B), and following a 2 minute reductive desorption of the immobilized nucleic acids (c). The bare electrodes display sigmoidal-shaped voltammograms, with 'plateau' currents, characteristic of ultramicroelectrode behavior. Significant suppression of the marker response (34% (A) and 26%(B) current diminutions at 0.0V), coupled to distorted voltlammograms (with steadily increasing currents), were observed following the adsorption of the ss-oligonucleotide and dsDNA, respectively. Incomplete suppressions of the marker response and a drawn out response were common at DNA-coated gold electrodes, and reflect the partial surface coverage and different surface structure organization. After holding the electrodes at −1.3 V for 2 minutes, the ferricyanide signals were restored to values approaching those of the bare microelectrode (c vs. a), reflecting the removal of the nucleicacid layer into the solution. The resulting voltammograms were drawn out, with slower electron-transfer kinetics indicative of an incomplete removal, possibly due to a remaining sulfur layer. The greater restoration of the current and shape with DNA reflect faster desorption kinetics. A control CV experiment, using the same potential and time sequences, but with a blank, rather than nucleic acid, solution, resulted in no change in the ferricyanide signal.

EXAMPLE 16
Effect of Different Desorption Potentials

Figure 10:
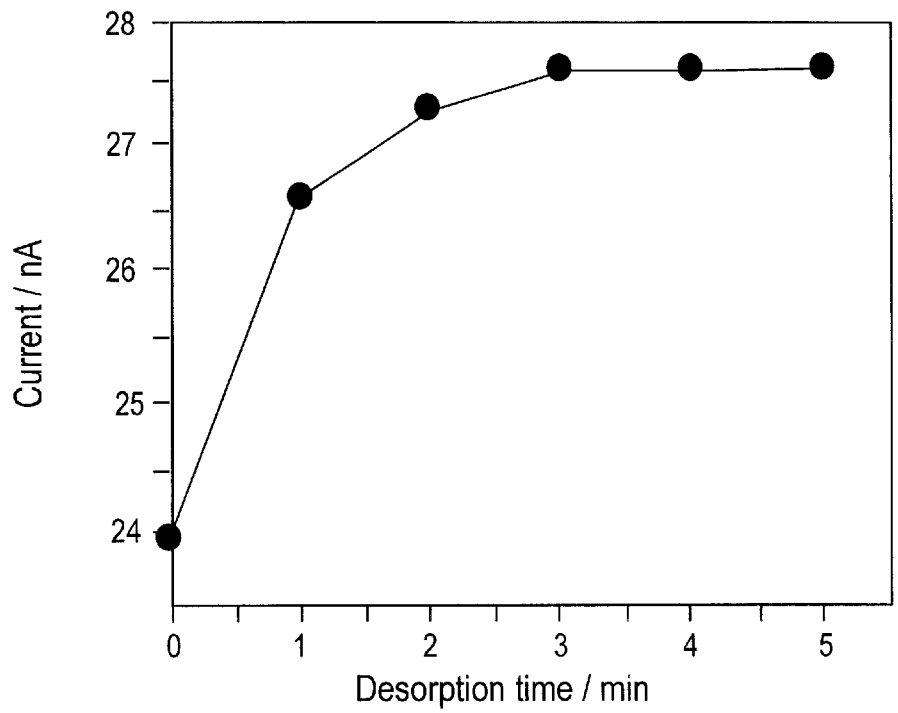
FIG. 10 depicts the effect of desorption time on the ferricyanide peak current at the dsDNA-coated gold microelectrode.

The effect of different desorption potentials upon the ferricyanide CV response and the QCM frequency change was evaluated using the electrode of Example 8 and methods and apparatus of Example 9. Both experiments yielded excellent agreement, with no current or frequency change for potentials more positive than −1.20 V (not shown). Increased currents and frequencies were observed between −1.20 V and −1.30 V, with the use of more negative potentials resulting in increasing background and noise levels associated with a hydrogen evolution reaction. A potential of −1.30 V was selected for all subsequent work. The large hydrogen evolution current, associated with the use of physiological pH, also influenced the direct cyclic voltammetric monitoring of the desorption peak. CV ferricyanide probing of the nucleic-acid adsorption/desorption processes at a 50 $\mu$m radius gold microelectrode (at 100 mV/s), yielded peak-shaped voltammograms, that were partially suppressed and restored following the adsorption and desorption, respectively. The shape of the curves following the desorption was nearly identical to those of the bare electrode, with minimal (5–10/mV) shifts of peak potentials. Changes in the ferricyanide peak current with the desorption time were used for monitoring the removal of the immobilized nucleic acid, as shown in FIG. 10. The reduction peak current increased rapidly up to one minute desorption, then more slowly, and approached steady state above 2 minutes. This profile is in excellent agreement with the EQCM desorption behavior shown in FIG. 6*b* where a steady state was attained within 115 seconds. While the profile of FIG. 10 indicates the ability to deliver small amounts of the genetic material at specific times, a slower or repeated release, over extended periods, may be desired for many practical applications. This may be accomplished through the use of different desorption potentials, passage of small cathodic currents, or the use of different interfacial environments.

EXAMPLE 17
EQCM Mass Changes with Non-Thiolated DNA

An EQCM apparatus was used as is generally described in Example 9 above. Calf thymus dsDNA and ssDNA were utilized as obtained. Gold QCM wafers were cleaned as generally described in Example 8 above. The surface was modified by casting 20 $\mu$L of a 1000 mg/L solution of either dsDNA or ssDNA containing 0.1 M Tris-HCl and 10 mM EDTA for 16 hours at 4° C. The surfaces were then washed with water and subsequently allowed to dry. Controlled blank crystal wafers were prepared in a similar fashion, except that the Tris-HCl/EDTA solution did not contain any DNA.

Figure 11:
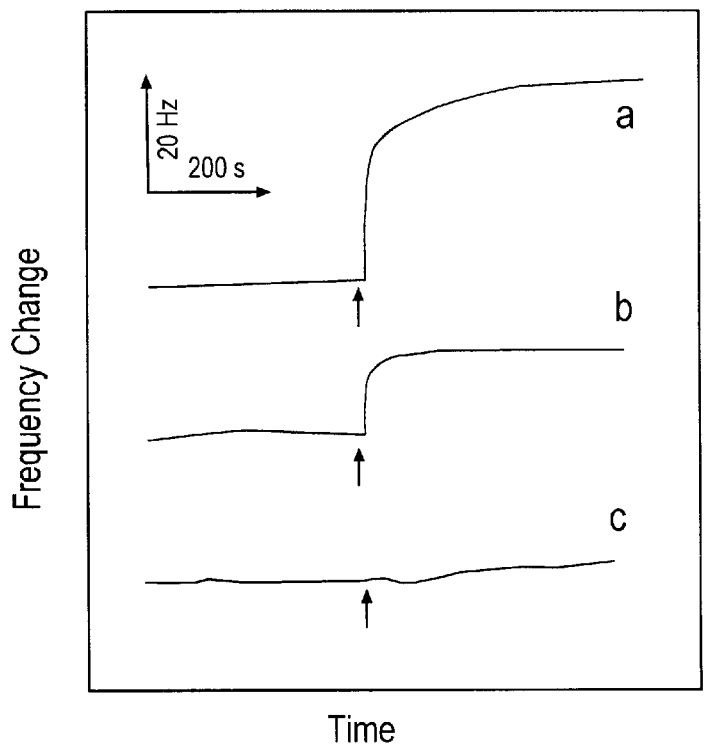
FIG. 11 depicts EQCM response on switching the potential from +0.4 V to −1.0 V for non-thiolated dsDNA and ssDNA.

FIG. 11 compares typical time-frequency QCM profiles for the dsDNA-(a) and ssDNA-(b) coated crystals, as well as for an uncoated crystal (c), recorded while stepping the potential from +0.40 V to −1.0 V, at the points indicated by the arrows. Both the nucleic-acid modified electrodes display a nearly instantaneous increase of the resonance frequency upon applying the negative potential. These changes reflect the decreased mass associated with the electrostatic repulsion of confined ssDNA and dsDNA. No frequency change is observed at the unmodified or control crystal. The fast attainment of steady-state frequency response following the potential step (75(*b*) and 330(*a*) seconds) indicates a rapid and complete removal of the DNA layer. No further frequency change was observed upon in a subsequent potential step from +0.40 V to −1.0 V. The steady-state frequency signals of FIG. 11, $\Delta$F of 34.4(a) and 13.9(b) Hz, correspond to mass changes of 644 and 261 ng/cm$^{-2}$ dsDNA and ssDNA, respectively.

EXAMPLE 18
Influence of Applied Potential on Non-Thiolated DNA Removal

Figure 12:
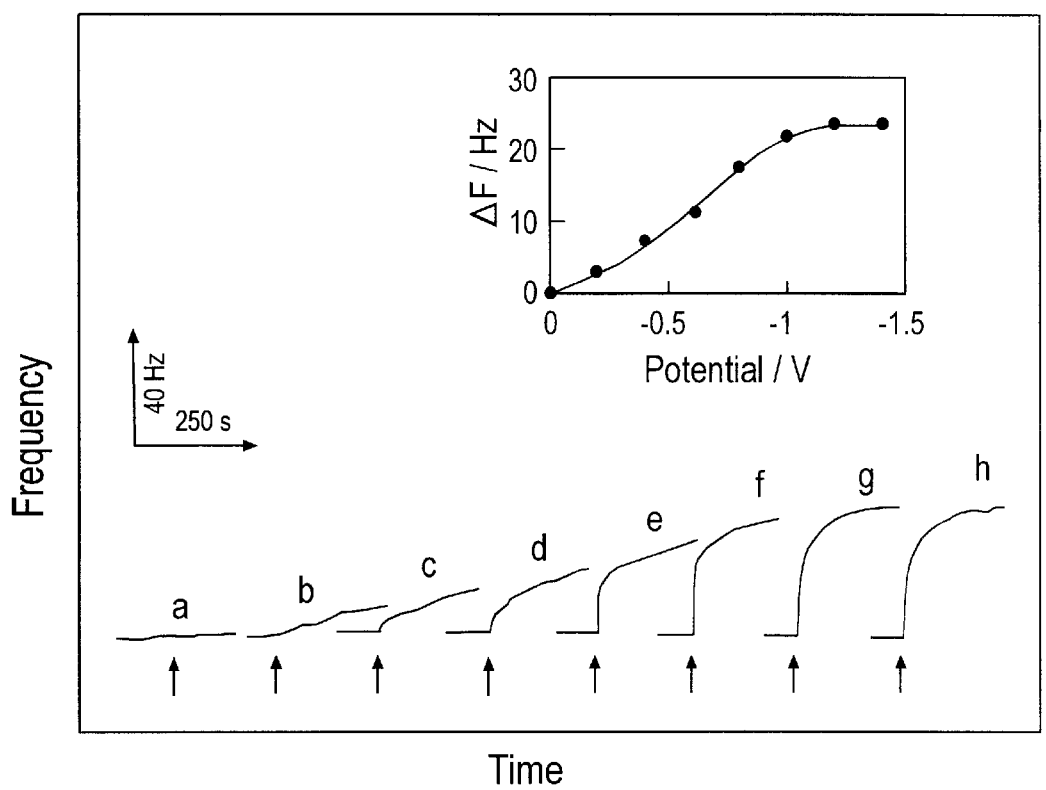
FIG. 12 depicts the effect of applied potential upon frequency response with non-thiolated DNA on a crystal.

The influence of the applied potential upon the efficiency of the electrochemically-induced DNA removal is shown in FIG. 12. Using the QCM crystal as in Example 17, experiments were conducted using a newly-prepared dsDNA immobilized crystal. The initial potential was +0.4 V, with a final potential of (a) 0.0 V; (b) −0.2 V; (c) −0.4 V; (d) −0.6 V; (e) −0.8 V; (f) −1.0 V; (g) −1.2 V; and (h) −1.4 V. The inset displays the corresponding frequency-change/potential profile; the frequency was measured 3 minutes after the step. As expected for electrostatic removal of anionic macromolecules, no release was observed at potentials more positive than −0.2 V (FIG. 12, a). The frequency change increases gradually upon raising the potential between −0.2 V and −1.0 V (FIGS. 2, b–f) to reach a constant value at more negative potentials (FIGS, 12, g,h). Such frequency changes (5–35 Hz) correspond to mass changes ranging from 94 to 655 ng cm$^{-2}$. A potential of −1.0 V was determined to be preferred for minimizing hydrogen evolution effects. The profiles observed in the low potential step experiments, a rapid frequency change followed by a slower one, without attainment of steady state, indicate that a fraction of the confined nucleic acids is more easily desorbed. This may be attributed to DNA being anchored to the gold surface by adsorption of both phosphate groups and the nitrogen-containing bases. The frequency-time profiles of FIG. 12 indicate also that low potentials (e.g., −0.2 V) can be used for a prolonged and sustained release of the immobilized DNA, over periods ranging from hours to days. Alternately, the use of short potential pulses to −1.0 V, for on the order of one to several seconds, coupled with longer intervals at +0.4 V, for on the order of several minutes or more, will permit release of repetitive doses over extended periods. This permits a point-wise construction of frequency-potential curves, as shown in FIG. 12, inset.

Figure 13:
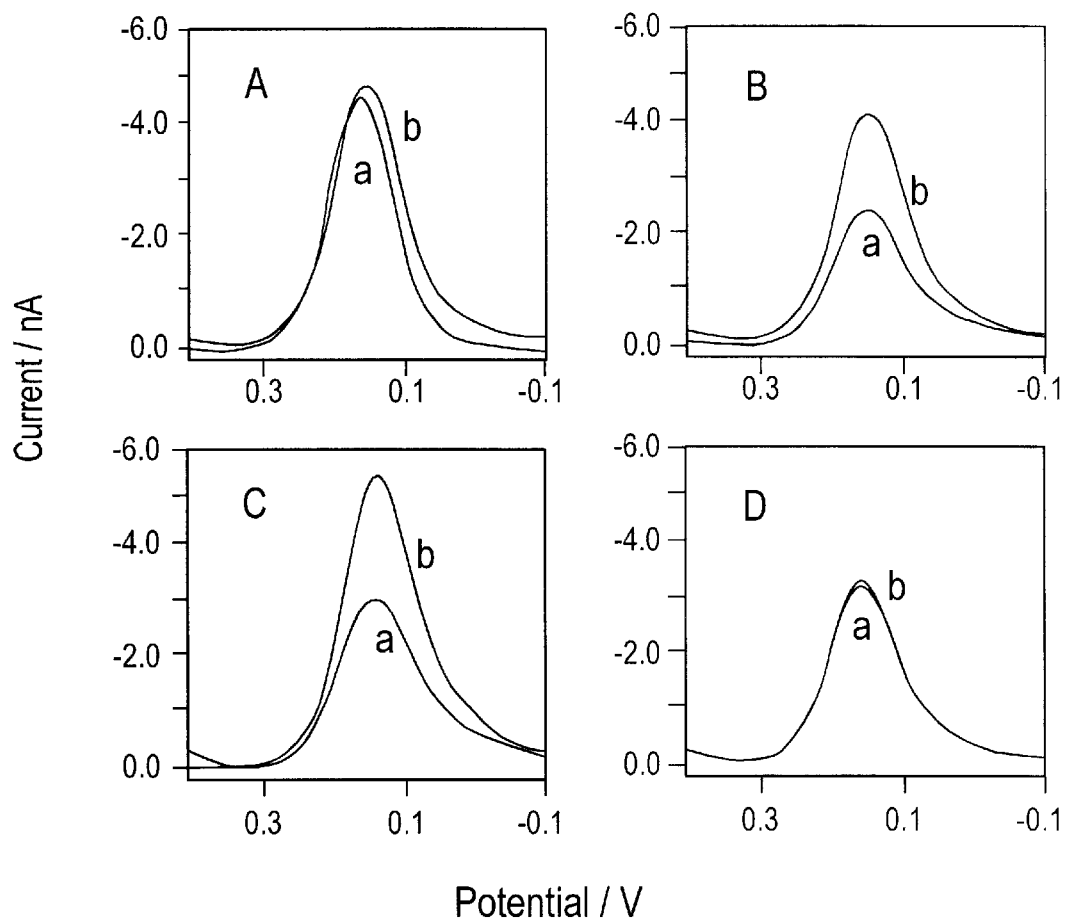
FIG. 13 depicts square-wave voltammograms for 1 mM potassium ferricyanide using different DNA-modified (B–D) and bare (A) gold microelectrodes before (a) and after (b) a 10 minute immersion in PBS at −1.2 V (A–C) or open circuit (D)

EXAMPLE 19
Voltammetric Blocking Experiments Using Non-Thiolated DNA and Ultramicroelectrodes A 12.5 $\mu$m radius gold microelectrode was used, as is generally described in Example 8, using the apparatus as generally described in Example 9. The gold microelectrodes were modified by a 16 hour immersion, at 4° C., in a 1,000 mg/L dsDNA (or ssDNA) solution containing 0.1M Tris-HCl and 10 mM EDTA. The modified surfaces were then washed with water and were allowed to dry. The desorption of the surface-confined DNA layer from the microelectrode was examined in a stirred PBS solution by applying the selected potential for different periods, usually −1.2 V for 10 minutes. The electrodes were then rinsed with water and transferred into a 1M KCl solution containing 1 mM of the $K_3Fe(CN)_6$ marker for subsequent voltammetric characterization. The square-wave voltammetric scan (from +0.4 V to −0.1 V) was recorded both before and after DNA desorption. All experiments were conducted at room temperature. In FIG. 13, (A) is a bare gold microelectrode, (B) is ssDNA, and (C) and (D) are dsDNA. Results are shown before (a) and after (b) a 10 minute immersion in PBS (0.05 M, pH 7.4) at −1.2 V (A–C) or open circuit (D). For each square-wave scan, the initial potential was +0.5 V, final potential was −0.1 V, the frequency was 30 Hz, the potential step was 1 mV and the amplitude was 25 mV. The adsorption accumulation of both ssDNA and dsDNA nucleic acids resulted in incomplete surface blocking, as shown in (a). Application of the desorption potential led to dramatic enhancements of ferricyanide peaks (b), approximately 80%, that reflect the release of the DNA layer. No change in the marker response is indicated from the corresponding control experiment, involving the use of open-circuit conditions (instead of −1.20 V)(D). FIG. 13 also includes the use of a bare gold microelectrode (A), demonstrating that the desorption conditions have a negligible effect upon the electroactivity of the ferricyanide marker.

EXAMPLE 20
Porous Reticulated Carbon Electrodes

To increase the surface area of the electrode, a porous reticulated vitreous carbon, which is a highly microporous network material, is employed. The nucleotide may be absorbed onto the carbon surface either prior to or subsequent to packing of the carbon network into a suitable structure. The carbon network is packed into a needle, tube or other similar structure. A conducting wire is inserted as in Example 1, or alternatively a conducting needle or tube is employed, and serves as the conducting wire. If not previously absorbed, the nucleotide is absorbed onto the carbon particles, optionally as described in Example 4.

EXAMPLE 21
EQCM Measurements with Lipid-Complexed Nucleotides

Figure 14:
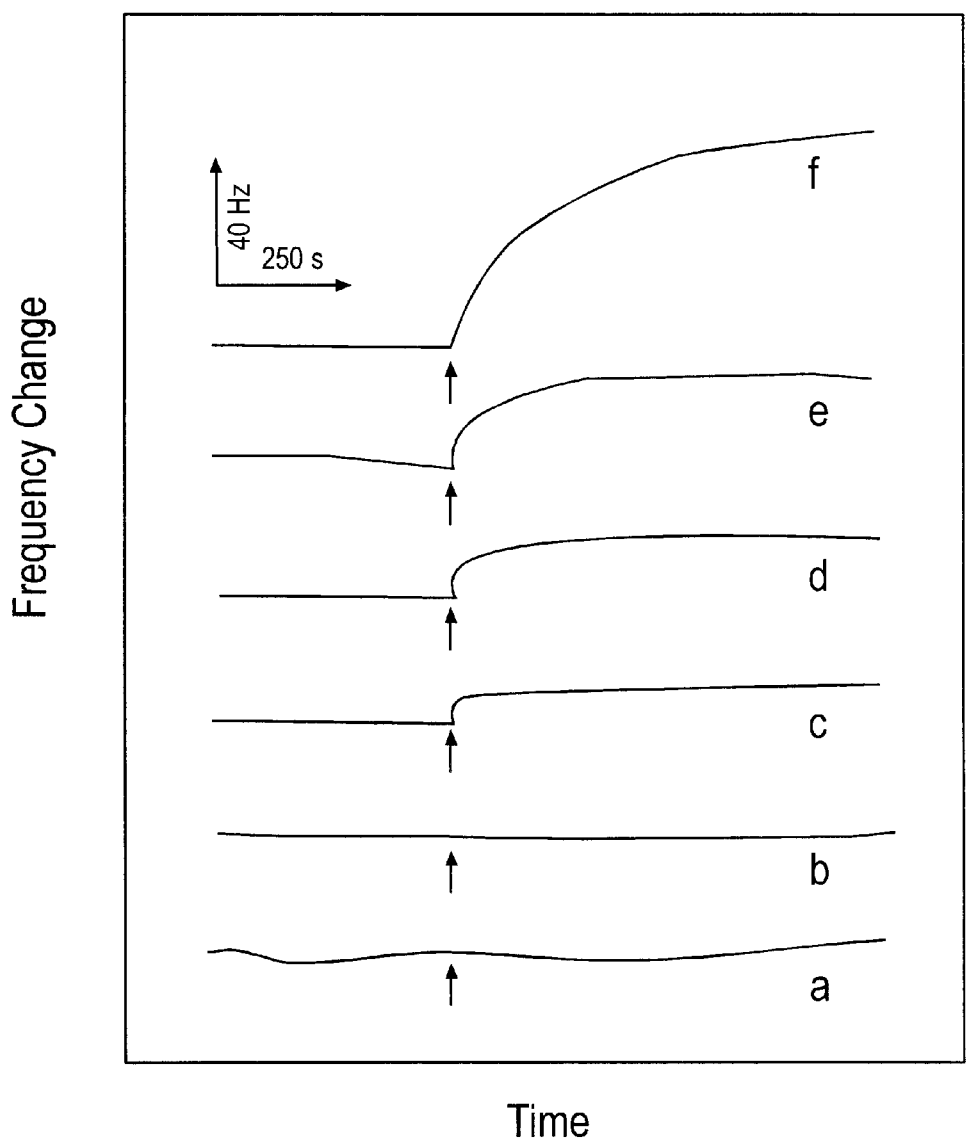
FIG. 14 depicts EQCM response on switching the potential from +0.4 V to −1.0 V for DNA and lipid complexes.

The method of Example 13 was generally employed, but using a variety of DNA and lipid complexes. LIPOFECTIN brand liposomes were employed, and the results are depicted on FIG. 14, where (a) is a blank crystal, (b) is LIPOFECTIN alone, (c) is DNA alone; (d) is a DNA and LIPOFECTIN complex at a 1:10 weight ratio; (e) is a DNA and LIPOFECTIN complex at a 1:12 weight ratio; and (f) is a DNA and LIPOFECTIN complex at a 1:40 weight ratio.

EXAMPLE 22
Reflectance FT-IR spectra of Upid-Complexed Nucleotides

Figure 15:
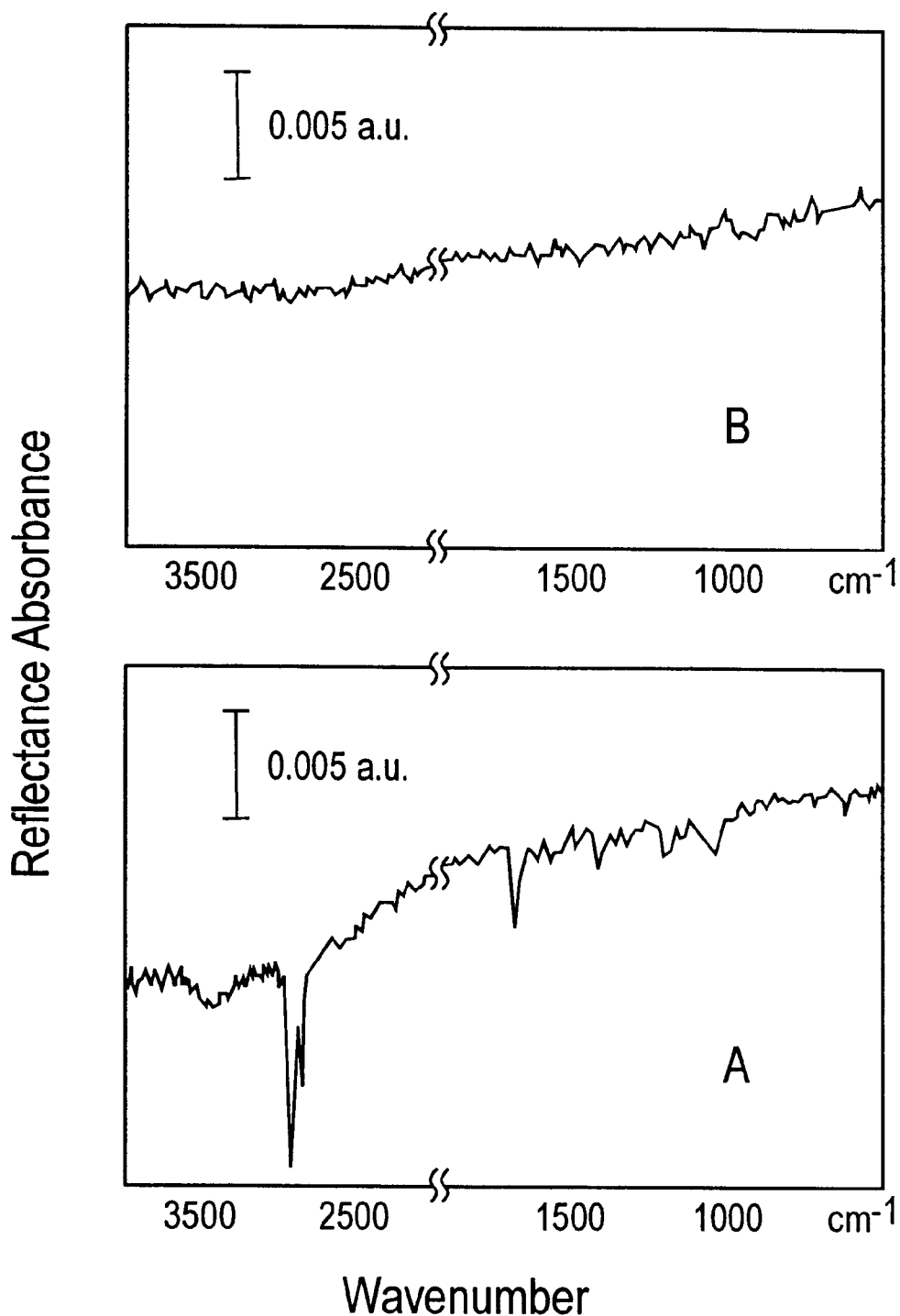
FIG. 15 depicts reflectance FT-IR spectra of a DNA and lipid complex-immobilized gold electrode before and after electrochemical release at a potential of −1.0 V for ten minutes.

A gold electrode of Example 9 was employed, cast with a 100 µL of a solution containing DNA and LIPOFECTIN brand lipid complexes, at a ratio of 1:20 DNA to LIPOFECTIN by weight on the surface of the electrode. FIG. 15 depicts the results before (A) and after (B) electrochemical release by application of−1.0 V potential for 10 minutes in a solution including 0.05 M PBS at pH 7.4. Further, adsorption bonds of the lipid-DNA complex disappear following electrochemical release.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A method for controlled release of nucleic acids, comprising the steps of:
    adsorbing nucleic acids to be released on at least one first electrode;
    providing a second electrode;
    immersing the first electrode and second electrode in an aqueous media in which the nucleic acids are to be released; and
    providing a negative electrical charge to the first electrode relative to the second electrode for a determined period of time sufficient to release at least a portion of the adsorbed nucleic acids over the period of time;
whereby the release of the nucleic acids is proportional to the relative electrical charge difference and period of persistence of the charge difference.

2. The method of claim 1, wherein the step of adsorbing further comprises applying a positive potential to the first electrode.

3. The method of claim 1, further comprising the step of providing a third electrode, wherein the second electrode serves as a counter electrode, and the third electrode serves as a reference electrode.

4. The method of claim 1, wherein the negative electrical charge is a potential difference of from about −0.02 V to about −1.4 V relative to the second electrode.

5. The method of claim 1, wherein the nucleic acids are in a nucleotide and lipid complex.

6. The method of claim 5, wherein the lipid is a liposome.

7. The method of claim 1, wherein the nucleic acids are thiolated.

8. The method of claim 1, wherein the nucleic acids are single-stranded DNA, double-stranded DNA, RNA or other nucleic acid.

9. The method of claim 1, wherein the nucleotide is an antisense nucleotide.

10. The method of claim 1, wherein the negative electrical charge is pulsed, thereby effecting incremental release of the nucleotide.

11. A method for controlled release of nucleic acids, comprising the steps of:
    adsorbing nucleic acids to be released on at least one first electrode;
    providing a second electrode;
    immersing the first electrode and second electrode in an aqueous media in which the nucleic acids are to be released;
    selecting a negative electrical charge to be applied to the first electrode relative to the second electrode, the negative electrical charge being sufficient to remove a portion, but less than all, of the adsorbed nucleic acids over a selected period of time;
    selecting a period of time for the negative electrical charge to be applied to the first electrode relative to the second electrode; and providing the negative electrical charge to the first electrode relative to the second electrode for the selected period of time, the negative electrical charge and period of time being sufficient to release a portion of the adsorbed nucleic acids.

12. The method of claim 11, wherein the step of adsorbing further comprises applying a positive potential to the first electrode.

13. The method of claim 11, further comprising the step of providing a third electrode, wherein the second electrode serves as a counter electrode, and the third electrode serves as a reference electrode.

14. The method of claim 11, wherein the negative electrical charge is a potential difference of from about −0.02 V to about −1.4 V relative to the second electrode.

15. The method of claim 11, wherein the nucleic acids are in a nucleic acid and lipid complex.

16. The method of claim 11, wherein the lipid is a liposome.

17. The method of claim 11, wherein the nucleic acids are thiolated.

18. The method of claim 11, wherein the nucleic acids comprises single-stranded DNA, double-stranded DNA or RNA.

19. The method of claim 11, wherein the nucleic acids comprise antisense nucleic acids.

20. The method of claim 11, wherein more than one period of time is selected for the negative electrical charge to be applied to the first electrode relative to the second electrode, such that the negative electrical charge is pulsed, thereby effecting incremental release of the nucleic acids with each pulse.

21. A method for controlled release of nucleic acids, comprising the steps of:

adsorbing one or more nucleic acids to be released, the nucleic acids comprising a structure between about a 25-mer oligonucleotide and a 350 base pair double-stranded nucleic acid, on at least one first electrode, the first electrode comprising a member selected from the group consisting of glassy carbon electrodes, carbon paste electrodes, metallic electrodes and metal-coated crystal wafer electrodes;

providing a second electrode;

immersing the first electrode and second electrode in a physiologically compatible aqueous media in which the nucleic acids are to be released;

selecting a negative electrical charge to be applied to the first electrode relative to the second electrode, the negative electrical charge being sufficient to remove a portion, but less than all, of the adsorbed nucleic acids over a selected period of time;

selecting a period of time for the negative electrical charge to be applied to the first electrode relative to the second electrode; and providing the negative electrical charge to the first electrode relative to the second electrode for the selected period of time, the negative electrical charge and period of time being sufficient to release a portion of the adsorbed nucleic acids.

22. The method of claim 21, wherein the step of adsorbing further comprises applying a positive potential to the first electrode.

23. The method of claim 21, further comprising the step of providing a third electrode, wherein the second electrode serves as a counter electrode, and the third electrode serves as a reference electrode.

24. The method of claim 21, wherein the negative electrical charge is a potential difference of from about −0.02 V to about −1.4 V relative to the second electrode.

25. The method of claim 21, wherein the nucleic acids are in a nucleic acid and lipid complex.

26. The method of claim 21, wherein the nucleic acids are thiolated.

27. The method of claim 21, wherein the nucleic acids comprise single-stranded DNA, double-stranded DNA or RNA.

28. The method of claim 21, wherein the nucleic acids comprise antisense nucleic acids.

29. The method of claim 21, wherein more than one period of time is selected for the negative electrical charge to be applied to the first electrode relative to the second electrode, such that the negative electrical charge is pulsed, thereby effecting incremental release of the nucleic acids with each pulse.

30. The method of claim 21, wherein the nucleic acid comprises DNA, the electrode comprises a member selected from the group consisting of carbon paste electrodes, gold electrodes, gold-coated quartz crystal electrodes and porous reticulated carbon electrodes, and the aqueous media comprises a phosphate buffer solution.

* * * * *